United States Patent [19]

Heitsch et al.

[11] Patent Number: 5,475,004
[45] Date of Patent: Dec. 12, 1995

[54] ANGIOTENSIN II RECEPTOR ANTAGONISTS FOR THE TREATMENT AND PROPHYLAXIS OF CORONARY HEART DISEASE

[75] Inventors: Holger Heitsch, Hofheim/Ts.; Gabriele Wiemer, Kronberg; Adalbert Wagner, Hattersheim/Main; Heinz-Werner Kleemann, Bad Homburg, all of Germany

[73] Assignee: Hoechst Aktiengesellschaft, Frankfurt am Main, Germany

[21] Appl. No.: 83,187

[22] Filed: Jun. 29, 1993

[30] Foreign Application Priority Data

Jul. 1, 1992 [DE] Germany .......................... 42 21 535.8
Aug. 27, 1992 [DE] Germany .......................... 42 28 555.0

[51] Int. Cl.⁶ ............................................... A61K 31/415
[52] U.S. Cl. ............................................................ 514/303
[58] Field of Search ................................................ 514/303

[56] References Cited

U.S. PATENT DOCUMENTS

| | | | |
|---|---|---|---|
| 4,355,044 | 10/1982 | Heller | 424/319 |
| 4,766,130 | 8/1988 | Austel et al. | 514/303 |
| 4,816,463 | 3/1989 | Blankley et al. | 514/293 |
| 4,880,804 | 11/1989 | Carini et al. | 514/234.5 |
| 5,332,744 | 7/1994 | Chakravarty et al. | 514/303 |
| 5,334,598 | 8/1994 | Bagley et al. | 514/303 |

OTHER PUBLICATIONS

Takehiko et al., CA 116:6558 (EP Pat. 434038, 26 Jun. 1991).

*Primary Examiner*—Johann Richter
*Assistant Examiner*—John Peabody
*Attorney, Agent, or Firm*—Finnegan, Henderson, Farabow, Garrett & Dunner

[57] ABSTRACT

Antagonists for angiotensin II receptors of the $AT_1$ subtype can be employed for the prophylaxis and combating of coronary heart disease.

Furthermore these compounds, such as, for example, azoles of the formula (I)

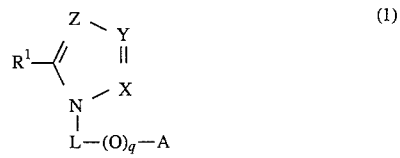

can also be used for the therapy of cognitive and erectile dysfunction.

4 Claims, 2 Drawing Sheets

ANGIOTENSIN II RECEPTOR ANTAGONISTS FOR THE TREATMENT AND PROPHYLAXIS OF CORONARY HEART DISEASE

The present invention relates to heterocyclic antagonists of specific angiotensin II receptors for use as medicines for the therapy of coronary heart disease such as, for example, of angina pectoris or of septic shock, and of cognitive and erectile dysfunction, as well as of renal and immunological disorders.

It is common to said disorders that they can be treated with substances which, in analogy to nitroglycerin for example, increase the NO level in the body. The described compounds increase endogenous NO production.

Imidazole-fused aromatic compounds are known inter alia from EP-A 399 731, EP-A 399 732, EP-A 400 835 and EP-A 434 038 as antagonists of angiotensin II receptors.

Imidazole derivatives and their use as antagonists of angiotensin II receptors are known from EP-A 28 834, EP-A 253 310, EP-A 401 030 and EP-A 324 377.

The present invention relates quite generally to the use of antagonists for angiotensin II receptors of the $AT_1$ subtype for combating the abovementioned disorders.

These specific $AT_1$ receptors are described by, for example, F. M. Bumpus et al. in Hypertension 17 (1991), pages 720 to 721.

Compounds of the formulae (I), (II), (III) and (IV), the structure and preparation of which are explained below, are particularly suitable as antagonists for this receptor subtype. Because of their metabolization, these compounds have proven to be particularly advantageous in humans.

Figure 1:
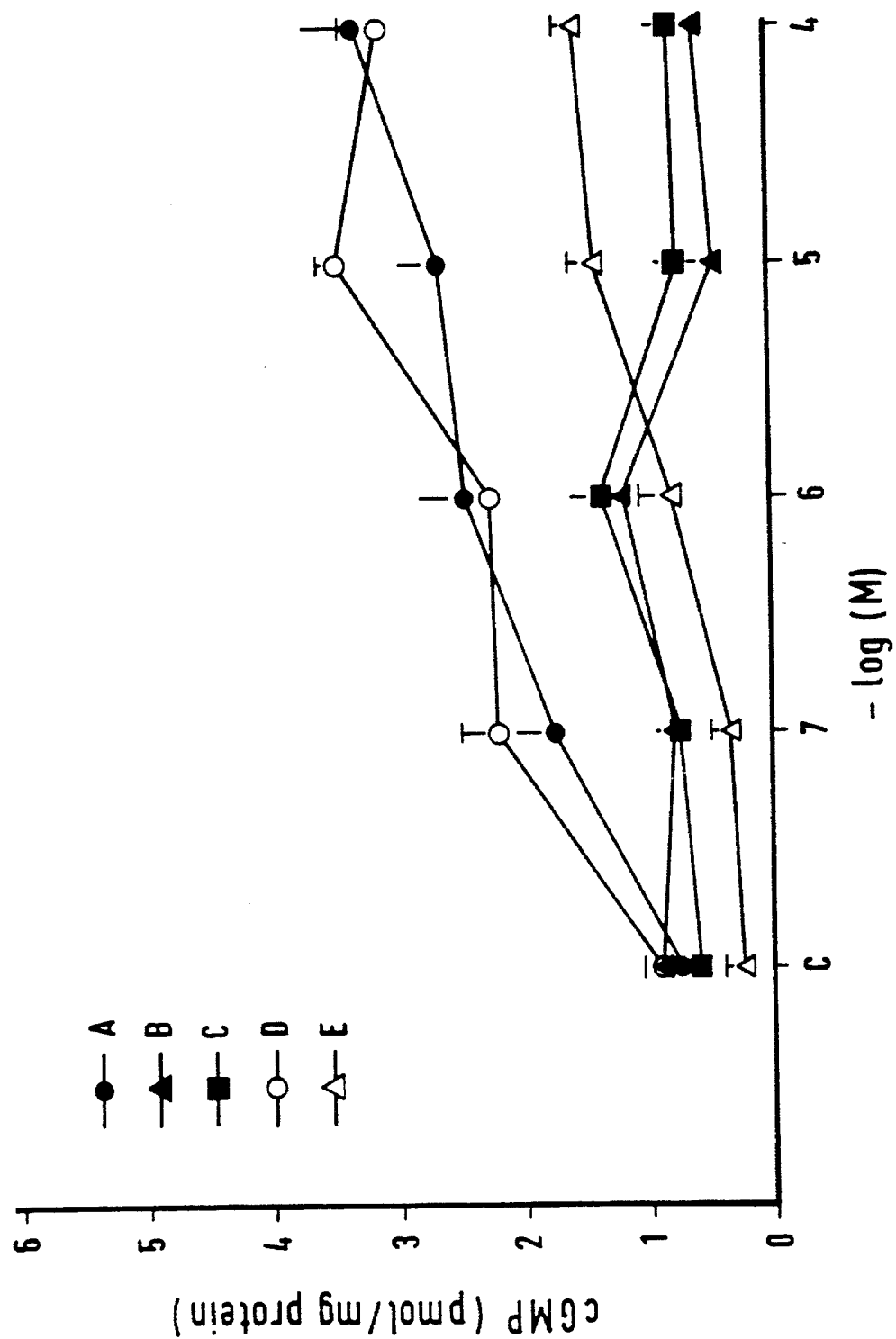
FIG. 1 depicts the effects of angiotensin II (D), three other compounds (B,C, and E) and a control (A) on endothelial cells of the bovine aorta with preincubation with the $AT_1$ receptor antagonist 2-n-butyl-4-chloro-1-[(2'-(1-tetrazol-5-yl)biphenyl-4-yl)methyl]imidazole-5-carboxylic acid.

The invention thus relates to the use of compounds of the formula (I)

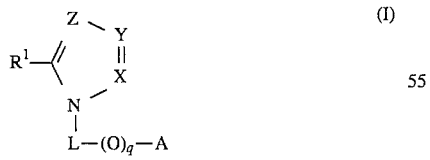

in which the symbols have the following meaning:
a) X, Y and Z are identical or different and are N or $CR^2$;
b) $R^1$ is
  1. $(C_1-C_{10})$-alkyl,
  2. $(C_3-C_{10})$-alkenyl,
  3. $(C_3-C_{10})$-alkynyl,
  4. —$OR^3$,
  5. $(C_3-C_8)$-cycloalkyl,
  6. $(C_4-C_{10})$-cycloalkylalkyl,
  7. $(C_5-C_{10})$-cycloalkylalkenyl,
  8. $(C_5-C_{10})$-cycloalkylalkynyl,
  9. —$(CH_2)_m$—B—$(CH_2)_n$—$R^4$,
  10. -benzyl
  11. a radical as defined under b) 1., 2., 3. or 9. which is monosubstituted by $CO_2R^3$,
  12. a radical as defined under b) 1., 2., 3. or 9. in which 1 to all the H atoms are replaced by fluorine or
  13. the radical defined under b) 10., which is substituted on the phenyl by 1 or 2 identical or different radicals from the series comprising halogen, $(C_1-C_4)$-alkoxy and nitro;
c) $R^2$ is
  1. hydrogen,
  2. halogen,
  3. nitro,
  4. $C_vF_{2v+1}$,
  5. pentafluorophenyl,
  6. cyano,
  7. —O—$R^6$,
  8. phenyl,
  9. phenyl-$(C_1-C_3)$-alkyl,
  10. $(C_1-C_{10})$-alkyl,
  11. $(C_3-C_{10})$-alkenyl,
  12. phenyl-$(C_2-C_6)$-alkenyl,
  13. 1-imidazolyl-$(CH_2)_m$—,
  14. 1,2,3-triazolyl-$(CH_2)_n$—,
  15. tetrazolyl-$(CH_2)_m$—,
  16. —$(CH_2)_{o-1}$—$CHR^7$—$OR^5$,
  17. —$(CH_2)_o$—O—CO—$R^3$,
  18. —$(CH_2)_o$—S—$R^6$,
  19. —$S(O)_r$—$R^{19}$,
  20. —CH=CH—$(CH_2)_m$—$CHR^3$—$OR^6$,
  21. —CH=CH—$(CH_2)_m$—CO—$R^8$,
  22. —CO—$R^8$,
  23. —CH=CH—$(CH_2)_m$—O—CO—$R^7$,
  24. —$(CH_2)_m$—$CH(CH_3)$—CO—$R^8$,
  25. —$(CH_2)_o$—CO—$R^8$,
  26.

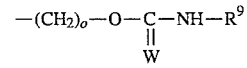

27.

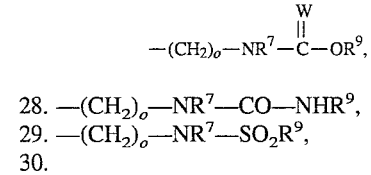

28. —$(CH_2)_o$—$NR^7$—CO—$NHR^9$,
  29. —$(CH_2)_o$—$NR^7$—$SO_2R^9$,
  30.

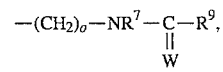

31. —$(CH_2)_n$F,
  32. —$(CH_2)_n$—O—$NO_2$,
  33. —$CH_2$—$N_3$,
  34. —$(CH_2)_n$—$NO_2$,
  35. —CH=N—$NR^5R^7$,
  36. phthalimido-$(CH_2)_n$—,

37.

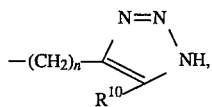

38.

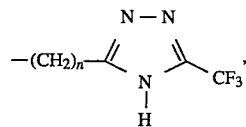

39.

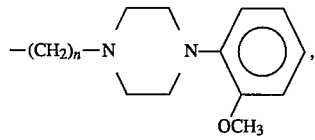

40.

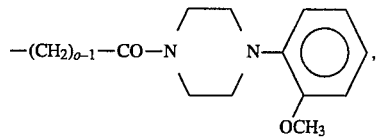

41. phenyl—SO$_2$—NH—N=CH—,
42.

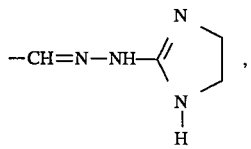

43. —(CH$_2$)$_n$—SO$_2$—NR$^7$—CS—NR$^6$R$^9$,
44. —(CH$_2$)$_n$SO$_2$—NR$^7$—CO—NR$^6$R$^9$,
45. —(CH$_2$)$_o$—SO$_2$R$^9$,
46. a radical as defined under c) 8. or 9., which is substituted on the phenyl by 1 or 2 identical or different radicals from the series comprising halogen, hydroxyl, methoxy, trifluoromethyl, CO$_2$R$^3$ and phenyl,
47. a radical as defined under c) 10., 11 or 19. in which one to all the H atoms are replaced by fluorine,
48. the radical defined under c) 14., which is substituted by 1 or 2 identical or different radicals from the series comprising methoxycarbonyl and (C$_1$–C$_4$)-alkyl,
49. —(CH$_2$)$_n$—SO$_2$—NR$^7$—CO—R$^6$ or
50. —(CH$_2$)$_n$—SO$_2$—NR$^7$CS—R$^6$;

d) R$^3$ is
1. hydrogen,
2. (C$_1$–C$_8$)-alkyl,
3. (C$_3$–C$_8$)-cycloalkyl,
4. phenyl,
5. benzyl or
6. the radical defined under d) 2. in which 1 to all the H atoms are replaced by fluorine;

e) R$^4$ is
1. hydrogen,
2. (C$_1$–C$_6$)-alkyl,
3. (C$_3$–C$_8$)-cycloalkyl,
4. (C$_2$–C$_4$)-alkenyl or
5. (C$_2$–C$_4$)-alkynyl;

f) R$^5$ is
1. hydrogen,
2. (C$_1$–C$_6$)-alkyl,
3. (C$_3$–C$_8$)-cycloalkyl,
4. phenyl or
5. benzyl;

g) R$^6$ and R$^9$ are identical or different and are
1. hydrogen,
2. (C$_1$–C$_6$)-alkyl, which can be substituted by 1 to 3 radicals from the series comprising (C$_1$–C$_6$)-alkoxy, which can be substituted in turn by 1–3 radicals from the series comprising hydroxyl, (C$_1$–C$_6$)-alkoxy, amino, mono-(C$_1$–C$_6$)-alkylamino and di-(C$_1$–C$_6$)-alkylamino, (C$_2$–C$_{10}$)-alkenyl, hydroxyl, amino, mono-(C$_1$–C$_6$)-alkylamino, di-(C$_1$–C$_6$)-alkylamino, (C$_1$–C$_6$)-alkoxycarbonylamino, (C$_6$–C$_{12}$)-aryl-(C$_1$–C$_4$)-alkoxycarbonylamino, (C$_6$–C$_{10}$)-aryl, (C$_6$–C$_{10}$)-aryl-(C$_1$–C$_3$)-alkyl, (C$_1$–C$_9$)-heteroaryl, carboxyl and (C$_1$–C$_4$)-alkoxycarbonyl,
3. (C$_3$–C$_8$)-cycloalkyl, in which the cycloalkyl part can be further substituted by 1–3 radicals from the series comprising (C$_1$–C$_4$)-alkyl and (C$_2$–C$_4$)-alkenyl,
4. (C$_3$–C$_8$)-cycloalkyl-(C$_3$–C$_3$)-alkyl,
5. (C$_6$–C$_{12}$)-aryl, preferably phenyl,
6. (C$_6$–C$_{10}$)-aryl-(C$_1$–C$_4$)-alkyl,
7. (C$_1$–C$_9$)-heteroaryl, which can be partly or completely hydrogenated,
8. a radical as defined under g) 5., 6., 7., 9., 15., 16., 17., 19., 20. or 21, which is substituted by one or two identical or different radicals from the series comprising halogen, hydroxyl, (C$_1$–C$_4$)-alkyl, methoxy, nitro, cyano, CO$_2$R$^3$, trifluoromethyl, NR$^{11}$R$^{12}$ and

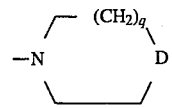

9. (C$_1$–C$_9$)-heteroaryl-(C$_1$–C$_3$)-alkyl, in which the heteroaryl part can be partly or completely hydrogenated,
10. (C$_1$–C$_6$)-alkyl, in which 1 to all the H atoms are replaced by fluorine,
11. (C$_2$–C$_{10}$)-alkenyl, (C$_2$–C$_{10}$)-alkenoyl or (C$_2$–C$_{10}$)-alkadienyl,
12. (C$_3$–C$_8$)-cycloalkenyl,
13. (C$_3$–C$_8$)-cycloalkenyl-(C$_1$–C$_6$)-alkyl,
14. bi- or tricyclic (C$_4$–C$_{10}$)-cycloalkenyl-(C$_1$–C$_4$)-alkyl, which can be further substituted by 1–3 (C$_1$–C$_4$)-alkyl radicals,
15. (C$_6$–C$_{10}$)-aryl-(C$_1$–C$_4$)-alkyl,
16. (C$_6$–C$_{10}$)-aryl-(C$_3$–C$_6$)-alkenyl,
17. (C$_1$–C$_9$)-hetaryl-(C$_3$–C$_6$)-alkenyl,
18. (C$_3$–C$_6$)-alkynyl,
19. (C$_6$–C$_{10}$)-aryl-(C$_3$–C$_6$)-alkynyl,
20. (C$_1$–C$_9$)-hetaryl-(C$_3$–C$_6$)-alkynyl or
21. R$^6$ and R$^9$, together with the N atom carrying them, are a hetaryl, which can also be partly or completely hydrogenated;

h) $R^7$ is
 1. hydrogen,
 2. $(C_1-C_6)$-alkyl,
 3. $(C_3-C_8)$-cycloalkyl,
 4. $(C_6-C_{12})$-aryl-$(C_1-C_6)$-alkyl, preferably benzyl,
 5. phenyl or
 6. $(C_1-C_9)$-heteroaryl;

i) $R^8$ is
 1. hydrogen,
 2. $(C_1-C_6)$-alkyl,
 3. $(C_3-C_8)$-cycloalkyl,
 4. phenyl-$(CH_2)_q$—,
 5. $OR^6$,
 6. $NR^{11}R^{12}$ or
 7.

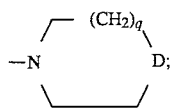

j) $R^{10}$ is cyano, nitro or $CO_2R^7$;

k) $R^{11}$ and $R^{12}$ are identical or different and are
 1. hydrogen,
 2. $(C_1-C_4)$-alkyl,
 3. phenyl,
 4. benzyl or
 5. α-methylbenzyl;

l) D is $NR^{13}$, O or $CH_2$;

m) $R^{13}$ is hydrogen, $(C_1-C_4)$-alkyl or phenyl;

n) A is a biphenyl radical, which can be substituted by up to 4, preferably up to 2, identical or different radicals $R^{14}$ or $R^{15}$;

o) $R^{14}$ is
 1. halogen,
 2. nitroso,
 3. nitro,
 4. amino,
 5. cyano,
 6. hydroxyl,
 7. $(C_1-C_6)$-alkyl,
 8. $(C_1-C_4)$-alkanoyl,
 9. $(C_1-C_4)$-alkanoyloxy,
 10. $CO_2R^3$,
 11. methanesulfonylamino,
 12. trifluoromethanesulfonylamino,
 13. —CO—NH—$OR^9$,
 14. —$SO_2$—$NR^6R^7$,
 15. —$CH_2$—$OR^7$,
 16. $(C_1-C_9)$-heteroaryl-$(CH_2)_q$—, preferably 1-tetrazolyl,
 17. $(C_7-C_{13})$-aroyl,
 18.

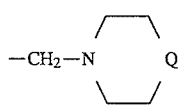

19.

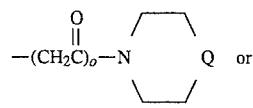

20. $(C_6-C_{12})$-aryl;

p) $R^{15}$ is
 1. hydrogen,
 2. $(C_1-C_6)$-alkyl,
 3. $(C_3-C_8)$-cycloalkyl,
 4. $(C_6-C_{12})$-aryl,
 5. $(C_7-C_{13})$-aroyl,
 6. $(C_1-C_4)$-alkoxy,
 7. $(C_1-C_4)$-alkanoyloxy,
 8. $(C_1-C_9)$-heteroaryl,
 9. $CO_2R^3$,
 10. halogen,
 11. cyano,
 12. nitro,
 13. $NR^6R^7$,
 14. hydroxyl,
 15. —CO—NH—$CHR^5$—$CO_2R^3$,
 16. sulfo,
 17. —$SO_3R^3$,
 18. —$SO_2$—$NR^7$—CO—$NR^6R^9$ or —$SO_2$—$NR^7$—CS—$NR^6R^9$,
 19. —$NR^7$—CO—$NR^6$—$SO_2$—$CH_2$—$R^5$,
 20. —$C(CF_3)_2OH$,
 21. phosphonooxy,
 22. —$PO_3H_2$,
 23. —NH—$PO(OH)_2$,
 24. —$S(O)_rR^6$,
 25. —CO—$R^8$,
 26. —CO—$NR^6R^9$,
 27. —$CR^{20}(OH)$—$PO(OH)_2$,
 28. the radical defined under o) 20.,
 29.

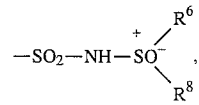

30.

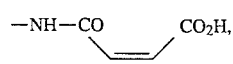

31.

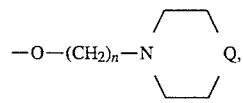

32. 5-tetrazolyl-NH—CO—,
33. —CO—NH—NH—$SO_2$—$CF_3$,

34.

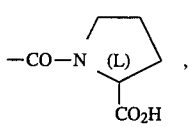,

35.

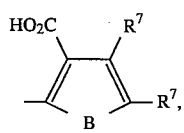

36.

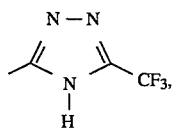

37.

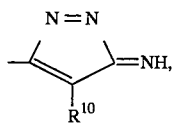

38.

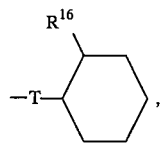,

39.

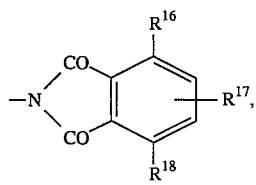

40. —CO—NH—SO$_2$—R$^{19}$,
41. —SO$_2$—NH—CO—R$^6$ or
42. the radical defined under p) 4., substituted by 1 or 2 identical or different radicals from the series comprising halogen, cyano, nitro, NR$^6$R$^7$ and hydroxyl; or
43. R$^{15}$, together with R$^{14}$, is —CO—NH—SO$_2$—,
44. —SO$_2$—NH—CO—O—R$^6$,
45. —SO$_2$—NH—SO$_2$—NR$^6$R$^9$ or
46. —SO$_2$—NH—SO$_2$—R$^6$;

q) B is O, NR$^7$ or S;
r) W is O or S;
s) L is (C$_1$–C$_3$)-alkanediyl;
t) R$^{16}$ is CO$_2$R$^3$ or CH$_2$CO$_2$R$^3$;

u) R$^{17}$ is hydrogen, halogen, (C$_1$–C$_4$)-alkyl or (C$_1$–C$_4$)-alkoxy;
v) R$^{18}$ is hydrogen, (C$_1$–C$_4$)-alkyl or phenyl;
w) R$^{19}$ is
  1. (C$_1$–C$_6$)-alkyl,
  2. (C$_3$–C$_8$)-cycloalkyl,
  3. phenyl,
  4. benzyl or
  5. the radical defined inder w) 1. in which 1 to all the H atoms are replaced by fluorine;
x) T is
  1. a single bond,
  2. —CO—,
  3. —CH$_2$—,
  4. —O—,
  5. —S—,
  6. —NR$^{21}$—,
  7. —CO—NR$^{21}$,
  8. NR$^{21}$—CO—,
  9. —O—CH$_2$—,
  10. —CH$_2$—O—,
  11. —S—CH$_2$—,
  12. —CH$_2$—S,
  13. —NH—CR$^{20}$R$^{22}$,
  14. —NR$^{21}$—SO$_2$,
  15. SO$_2$—NR$^{21}$—,
  16. —CR$^{20}$R$^{22}$—NH,
  17. —CH=CH—,
  18. —CF=CF—,
  19. —CH=CF—,
  20. —CF=CH—,
  21. —CH$_2$—CH$_2$—,
  22. —CF$_2$—CF$_2$—,
  23. —CH(OR$^3$)—,
  24. —CH(OCOR$^5$)—,
  25.

or
  26.

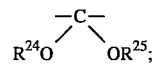;

y) R$^{20}$ and R$^{22}$ are identical or different and are hydrogen, (C$_1$–C$_5$)-alkyl, phenyl, allyl or benzyl;
z) R$^{21}$ is hydrogen, (C$_1$–C$_6$)-alkyl, benzyl or allyl;
a') R$^{23}$ is
  1. NR$^{20}$R$^{21}$,
  2. ureido,
  3. thioureido,
  4. toluene-4-sulfonyl or
  5. benzenesulfonylamino;
b') R$^{24}$ and R$^{25}$ are identical or different and are (C$_1$–C$_4$)-alkyl, or together are —(CH$_2$)$_q$—;
c') Q is CH$_2$, NH, O or S;
d') m is an integer from 0 to 5;
e') n is an integer from 1 to 5;
f') o is an integer from 1 to 10;
g') q is 0 or 1;
h') r is 0, 1 or 2 and i') v is an integer from 1 to 6;
and physiologically tolerated salts thereof.

Alkyl, alkenyl and alkynyl can be straight-chain or branched. The same applies to radicals derived therefrom, such as alkanoyl or alkoxy. Cycloalkyl is also understood as meaning alkyl-substituted rings. $(C_6-C_{12})$-Aryl is, for example, phenyl, naphthyl or biphenylyl, preferably phenyl. The same applies to radicals derived therefrom, such as aroyl and aralkyl.

$(C_1-C_9)$-heteroaryl is understood as meaning, in particular, radicals which are derived from phenyl or naphthyl, in which one or more CH groups are replaced by N and/or in which at least two adjacent CH groups are replaced by S, NH or O (to form a five-membered aromatic ring). Furthermore, one or both the atoms of the condensation point of bicyclic radicals can also be N atoms (as in indolizinyl).

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl or cinnolinyl.

Any stereocenters which occur can be in both the (R) and the (S) configuration.

A is linked via an alkanediyl bridge L, which is preferably a methylene group. The methylene group is preferably bonded directly to the biphenyl radical. Physiologically tolerated salts of compounds of the formula (I) are understood as meaning both organic and inorganic salts thereof, such as are described in Remington's Pharmaceutical Sciences (17th Edition, page 1418 (1985)). The sodium, potassium, calcium and ammonium salts, inter alia, are preferred for acids groups because of their physical and chemical stability and solubility; the salts of hydrochloric acid, sulfuric acid, phosphoric acid or carboxylic acids or sulfonic acids, such as, for example, acetic acid, citric acid, benzoic acid, maleic acid, fumaric acid, tartaric acid and p-toluenesulfonic acid, inter alia are preferred for basic groups.

Compounds of the formula (I) which are furthermore preferably employed in the treatment and prophylaxis of the disorders mentioned are those in which X is N, Y is $CR^2$ and Z is $CR^2$;

X is $CR^2$, Y is N and Z is $CR^2$;

X is $CR^2$, Y is $CR^2$ and Z is N or

X, Y and Z are each N, a) $R^1$ is
1. $(C_1-C_{10})$-alkyl,
2. $(C_3-C_{10})$-alkenyl,
3. $(C_3-C_{10})$-alkynyl,
4. $(C_1-C_8)$-cycloalkyl,
5. benzyl or
6. benzyl, which is substituted as described above (b 13.);

b) $R^2$ is
1. hydrogen,
2. halogen,
3. nitro,
4. $C_vF_{2v+1}$,
5. pentafluorophenyl,
6. cyano,
7. —O—$R^6$,
8. phenyl,
9. phenyl-$(C_1-C_3)$-alkyl,
10. $(C_1-C_{10})$-alkyl,
11. $(C_3-C_{10})$-alkenyl,
12. phenyl-$(C_2-C_6)$-alkenyl,
13. 1-imidazolyl-$(CH_2)_m$—,
14. 1,2,3-triazolyl-$(CH_2)_o$—,
15. tetrazolyl-$(CH_2)_m$—,
16. —$(CH_2)_o$—1—$CHR^7$—$OR^5$,
17. —$(CH_2)_o$—O—$COR^3$,
18. —$COR^8$,
19. —$(CH_2)_o$—(CO—$R^8$
20. —$S(O)_rR^{19}$,
21. —CH=CH—$(CH_2)_m$—$CHR^3$—$OR^6$,
22. —CH=CH—$(CH_2)_m$—CO—$R^8$,
23. —$(CH_2)_o$—NH—CO—$OR^9$,
24. —$(CH_2)_o$—NH—$SO_2$—$R^9$,
25. —$(CH_2)_n$F,
26. —$(CH_2)_o$—$SO_3R^9$,
27. —$(CH_2)_n$—$SO_2$—NH—CO—$NR^6R^9$,
28. —$(CH_2)_n$—$SO_2$—NH—CS—$NR^6R^9$, or
29. a radical as defined under b) 8., 9., 10., 11 or 14, which is substituted as above under c) 46., 47. or 48. in each case as described for such a radical,
30. —$(CH_2)_n$—$SO_2$—$NR^7$—CO—$R^6$ or
31. —$(CH_2)_n$—$SO_2$—$NR^7$—CS—$R^6$;

c) $R^8$ is hydrogen, $(C_1-C_5)$-alkyl, $OR^6$, $NR^{11}R^{12}$ or morpholino;

d) T is
1. a single bond,
2. —CO—,
3. —$CONR^{21}$—,
4. —$CH_2$—$CH_2$—,
5. —$NR^{21}$—CO—,
6. —O—$CH_2$—,
7. —$CH_2$—O—,
8. —S—$CH_2$—,
9. —$CH_2$—S—,
10. —NH—$CH_2$—,
11. —$CH_2$—NH— or
12. —CH=CH— and the other radicals and variables are as defined above.

Particularly preferred compounds of the formula (I) are those in which:

X is N, Y is $CR^2$ and Z is $CR^2$;

X is $CR^2$, Y is N and Z is $CR^2$;

X is $CR^2$, Y is $CR^2$ and Z is N or

X, Y and Z are each N, a) $R^1$ is $(C_1-C_7)$-alkyl, $(C_3-C_{10})$-alkenyl or $(C_3-C_7)$-alkynyl;

b) $R^2$ is
1. chlorine,
2. bromine,
3. $C_vF_{2v+1}$, where v=1, 2 or 3,
4. pentafluorophenyl,
5. O—$R^6$,
6. —$S(O)_rR^{19}$,
7. $(CH_2)_o$—1—$CHR^7$—$OR^5$,
8. $(CH_2)_o$—O—CO—$R^3$,
9. —$COR^8$,
10. —$(CH_2)_o$—CO—$R^8$,
11. —$CH_2$—NH—CO—$R^8$,
12. —$(CH_2)_o$—NH—$SO_2$—$R^9$,
13. —CH=CH—$CHR^3$—$OR^6$,
14. tetrazolyl—$(CH_2)_m$—,
15. —$(CH_2)_nSO_2$—NH—CO—$NR^6R^9$,
16. —$(CH_2)_o$—$SO_3R^9$ or $(C_1-C_6)$-alkyl which is optionally substituted by hydroxyl, preferably hydroxymethyl;

c) $R^3$ is hydrogen, $(C_1-C_4)$-alkyl or benzyl;

d) $R^6$ and $R^9$ are identical or different and are
1. hydrogen,
2. $(C_1-C_6)$-alkyl, which can be substituted by 1 to 3 radicals from the series comprising $(C_1-C_6)$-alkoxy, which can be substituted in turn by 1 to 3 radicals from the series comprising hydroxyl, $(C_1-C_6)$-alkoxy, amino, mono-$(C_1-C_6)$-alkylamino and di-$(C_1-C_6)$-alkylamino, $(C_2-C_{10})$-alkenyl, hydroxyl, amino, mono-$(C_1-C_6)$-alkylamino, di-$(C_1-C_6)$-alkylamino, $(C_1-C_6)$-alkoxycarbonylamino, $(C_6-C_{12})$-aryl-$(C_1-C_4)$-alkoxycarbonylamino, $(C_6-C_{10})$-aryl, $(C_6-C_{10})$-aryl-$(C_1-C_3)$-alkyl, $(C_1-C_9)$-heteroaryl, carboxyl and $(C_1-C_4)$-alkoxycarbonyl,
3. $(C_1-C_6)$-cycloalkyl,
4. $(C_3-C_6)$-cycloalkyl-$(C_1-C_3)$-alkyl,
5. phenyl,
6. phenyl-$(C_1-C_3)$-alkyl,
7. $(C_1-C_7)$-heteroaryl, which can be partly or completely hydrogenated,
8. a radical as defined above under g) 5., 6., 7. or 9., 14. to 16. and 18. to 20., substituted by 1 or 2 identical or different radicals from the series comprising halogen, hydroxyl, $(C_1-C_4)$-alkyl, methoxy, nitro, cyano, $CO_2R^3$, trifluoromethyl, $-NR^{11}R^{12}$ and

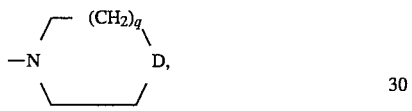

9. $(C_1-C_9)$-heteroaryl-$(C_1-C_3)$-alkyl, in which the heteroaryl part can be partly or completely hydrogenated,
10. $(C_1-C_6)$-alkyl, in which 1 to all the H atoms are replaced by fluorine,
11. $(C_2-C_4)$-alkenyl or $(C_3-C_6)$-alkenoyl,
12. $(C_3-C_6)$-cycloalkenyl,
13. $(C_3-C_6)$-cycloalkenyl-$(C_1-C_3)$-alkyl,
14. bi- or tricyclic $(C_4-C_{10})$-cycloalkenyl-$(C_1-C_{10})$-alkyl, which can also be substituted by 1 to 3 $(C_1-C_4)$-alkyl radicals,
15. $(C_6-C_{10})$-aryl-$(C_1-C_3)$-alkyl,
16. $(C_6-C_{10})$-aryl-$(C_3-C_6)$-alkenyl,
17. $(C_1-C_6)$-hetaryl-$(C_3-C_6)$-alkenyl,
18. $(C_3-C_6)$-alkynyl,
19. $(C_6-C_{10})$-aryl-$(C_3-C_6)$-alkynyl,
20. $(C_1-C_6)$-hetaryl-$(C_3-C_6)$-alkynyl or
21. $R^6$ and $R^9$, together with the N atom carrying them, are a hetaryl, which can also be partly or completely hydrogenated;

e) $R^7$ is hydrogen, $(C_1-C_4)$-alkyl, $(C_1-C_9)$-heteroaryl or $(C_6-C_{12})$-aryl-$(C_1-C_4)$-alkyl;

f) $R^{14}$ is
1. $(C_1-C_4)$-alkyl,
2. $(C_1-C_4)$-alkoxy,
3. cyano,
4. amino,
5. nitroso,
6. nitro,
7. fluorine,
8. chlorine,
9. bromine,
10. $(C_1-C_9)$-heteroaryl-$CH_2-$,
11. $(C_1-C_4)$-alkanoyloxy,
12. $(C_1-C_4)$-alkanoyl,
13. benzoyl,
14. $-NH-CO-R^7$ or
15. tetrazolyl;

h) $R^{15}$ is
1. $(C_1-C_4)$-alkyl,
2. $(C_6-C_{12})$-aryl,
3. $(C_1-C_3)$-alkanoyloxy,
4. $(C_1-C_4)$-alkoxy,
5. $(C_1-C_9)$-heteroaryl, preferably 5-tetrazolyl,
6. cyano,
7. nitro,
8. hydroxyl,
9. $-S(O)_rR^6$,
10. $-SO_3R^3$,
11. chlorine,
12. bromine,
13. benzoyl,
14. $-CO_2R^3$,
15. $-CO-NH-R^6$,
16. $-CO-R^8$,
17. $-SO_2-NR^6R^7$,
18. $-SO_2-NH-CO-NR^6R^9$,
19. $-PO_3H_2$,
20. $-CO-CHR^5-CO_2H$,
21. $-NH-CO-NH-SO_2-CH_2-R^5$,
22. 5-tetrazolyl-$NH-CO-$,
23.

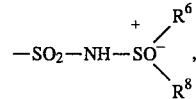

24.

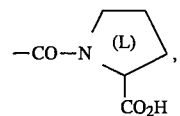

25.

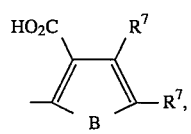

26.

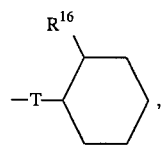

27.

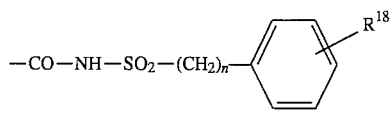

or 28. the radical defined under h) 2., substituted as defined above (see p) 42.) or
29. $R^{15}$ together with $R^{14}$ is —CO—NH—SO$_2$—,
30. —SO$_2$—NH—COO—R$^6$—,
31. —SO$_2$—NH—SO$_2$—NR$^6$R$^9$ or
32. —SO$_2$—NH—SO$_2$—R$^6$;

i) $R^{18}$ is hydrogen, methyl or ethyl;

j) T is a single bond, —O—, —CO—, —NHCO— or —OCH$_2$—; and k) q=0 and L=methylene, and the other radicals and variables are as defined above.

Compounds which are moreover preferred are azole derivatives of the general formula (I) in which Z is a nitrogen atom, Y and X independently of one another are $CR^2$ and the other symbols are as defined above.

Compounds which are particularly suitable are furthermore azole derivatives of the general formula (I) in which the symbols have the following meaning:

Z is nitrogen,

X and Y independently of one another are $CR^2$, $R^1$ is (C$_1$–C$_7$)-alkyl, (C$_3$–C$_7$)-alkenyl or (C$_3$–C$_7$)-alkynyl, $R^2$ is hydrogen, halogen, nitro, (C$_1$–C$_3$)-perfluoroalkyl, cyano, (C$_1$–C$_{10}$)-alkyl, (C$_3$–C$_{10}$)-alkenyl, —CH$_2$OR$^5$, —S(O)$_r$—R$^{19}$, —CO—R$^8$ or —O—R$^6$, $R^5$ is hydrogen or (C$_1$–C$_6$)-alkyl, $R^6$ and $R^9$ are
1. hydrogen,
2. (C$_1$–C$_6$)-alkyl, which can be substituted by 1 to 3 radicals from the series comprising (C$_1$–C$_6$)-alkoxy, which can be substituted in turn by 1 to 3 radicals from the series comprising hydroxyl, (C$_1$–C$_6$)-alkoxy, amino, mono-(C$_1$–C$_6$)-alkylamino and di-(C$_1$–C$_6$)-alkylamino, (C$_2$–C$_{10}$)-alkenyl, hydroxyl, amino, mono(C$_1$–C$_6$)-alkylamino, di-(C$_1$–C$_6$)-alkylamino, (C$_1$–C$_6$)-alkoxycarbonylamino, (C$_6$–C$_{10}$)-aryl, (C$_6$–C$_{10}$)-aryl-(C$_1$–C$_3$)-alkyl, (C$_1$–C$_9$)-heteroaryl, carboxyl and (C$_1$–C$_4$)-alkoxycarbonyl;
3. (C$_3$–C$_8$)-cycloalkyl,
4. (C$_3$–C$_6$)-cycloalkyl-(C$_1$–C$_4$)-alkyl,
5. (C$_6$–C$_{12}$)-aryl, preferably phenyl,
6. (C$_6$–C$_{10}$)-aryl- (C$_1$–C$_4$)-alkyl,
7. (C$_1$–C$_9$)-heteroaryl, which can be partly or completely hydrogenated,
8. (C$_1$–C$_9$)-heteroaryl-(C$_1$–C$_3$)-alkyl, in which the heteroaryl part can be partly or completely hydrogenated,
9. a radical as defined above under 5., 6., 7. and 8., substituted by 1 or 2 identical or different radicals from the series comprising halogen, hydroxyl, (C$_1$–C$_4$)-alkyl, methoxy, nitro, cyano, CO$_2$R$^3$, trifluoromethyl, -NR$^{11}$R$^{12}$ and

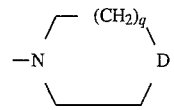

10. (C$_1$–C$_6$)-alkyl, in which 1 to all the H atoms are replaced by fluorine,
11. (C$_2$–C$_6$)-alkenyl or (C$_3$–C$_6$)-alkenoyl,
12. (C$_1$–C$_6$)-cycloalkenyl,
13. (C$_3$–C$_8$)-cycloalkenyl-(C$_1$–C$_3$)-alkyl,
14. (C$_6$–C$_{10}$)-aryl-(C$_1$–C$_4$)-alkyl,
15. (C$_6$–C$_{10}$)-aryl-(C$_3$–C$_6$)-alkenyl,
16. (C$_1$–C$_9$)-hetaryl-(C$_3$–C$_6$)-alkenyl,
17. (C$_3$–C$_6$)-alkynyl,
18. (C$_6$–C$_{10}$)-aryl-(C$_3$–C$_6$)-alkynyl,
19. (C$_1$–C$_9$)-hetaryl-(C$_3$–C$_6$)-alkynyl, or
20. $R^6$ and $R^9$, together with the N atom carrying them, are a hetaryl, which can also be partly or completely hydrogenated, $R^7$ is hydrogen, $R^8$ is hydrogen or —OR$^6$, $R^{11}$ and $R^{12}$ independently of one another are hydrogen or (C$_1$–C$_4$)-alkyl, D is —NR$^{13}$, —O or —CH$_2$, $R^{13}$ is hydrogen or (C$_1$–C$_4$)-alkyl, A is a biphenyl radical, which is substituted by a radical $R^{15}$ or by $R^{14}$ and $R^{15}$ together, $R^{15}$ is —SO$_2$—NR$^7$—CO—NR$^6$R$^9$, —SO$_2$—NH—COO—R$^6$, —SO$_2$—NH—SO$_2$—NR$^6$—R$^9$, —SO$_2$—NH—CO—R$^6$ or —SO$_2$—NH—SO$_2$—R$^6$; or $R^{14}$ and $R^{15}$ together can be —CO—NH—SO$_2$—, L is —CH$_2$—, q is zero and r is zero, 1 or 2, and physiologically tolerated salts thereof.

Compounds of the formula (I) and physiologically tolerated salts thereof can be prepared by alkylating compounds of the formula (IIa)

in which $R^1$X, Y, and Z are as defined above, with compounds of the formula (IIIa)

in which L, A and q are as defined above and U is a leaving group, splitting off again any protective groups temporarily introduced, if appropriate converting the resulting sulfonamides of the formula (I) into urethanes of the formula (I), converting resulting sulfonamides of the formula (I) or resulting urethanes of the formula (I), and if appropriate converting the resulting compounds of the formula (I) into their physiologically tolerated salts.

Suitable leaving groups U are preferably nucleofugic groups (cf. Angew. Chem. 72 [1960] 71), such as halogen, o-toluenesulfonate, mesylate or triflate.

Processes for the preparation of the precursors of the formula (IIa) are known, inter alia, from U.S. Pat. No. 4,355,044, EP-A-324 377 and EP-A-323 841.

Other processes are described by G. L'abbe (Chem. Rev. 69,345 [1969]), T. Srodsky ("The Chemistry of the Azido Group", Wiley, New York, 1971, page 331), H. Wamhoff ("Comprehensive Heterocyclic Chemistry) and by S. Katritzky Ed., Pergamon Press, New York [1984]).

Another process for the preparation of compounds of the formula (IIa) starts from 1-cyanoglyoxylic acid 2-oxime derivatives and, after reduction of the oxime by reducing agents which are known from the literature and addition of mercapto compounds onto the nitrile group using suitable protective groups, gives precursors which can be cyclized to imidazoles under dehydrating conditions. Mixtures of $PCl_5$ and dimethylaminopyridine (DMAP), $POCl_3$ and $SOCl_2$ and mixtures thereof with DMAP, inter alia, can be used for the cyclization step.

The oxidation of the thio compounds of the formula (I) where $R^2$ is $—S(O)_rR^{19}$, in which r is zero or 1, to give the corresponding sulfones and sulfoxides is preferably carried out using peracids in suitable solvents, such as, for example, methylene chloride.

Corresponding benzyl halides, tosylates, mesylates or triflates or corresponding alkyl halides, tosylates, mesylates or triflates, for example, are suitable for alkylation of the azoles of the formula (IIa).

The alkylation is carried out in an analogous manner to processes which are known in principle.

Azole derivatives of the formula (IIa) are metallized, for example, in the presence of a base. Preferred bases are metal hydrides of the formula MH, such as, for example, lithium hydride, sodium hydride or potassium hydride, in, for example, dimethylformamide or dimethyl sulfoxide as a solvent, or metal alkoxides of the formula MOR, in which R is methyl, ethyl or t-butyl, and the reaction is carried out in the corresponding alcohol, dimethylformamide or dimethyl sulfoxide. The azole salts thus formed are dissolved in an aprotic solvent, such as dimethylformamide or dimethyl sulfoxide, and a suitable amount of alkylating reagent is added.

An alternative possibility for the deprotonation of the azole derivatives is, for example, reaction with potassium carbonate in dimethylformamide or dimethyl sulfoxide.

The reactions are carried out at temperatures below room temperature up to the boiling point of the reaction mixture, preferably between +20° C. and the boiling point of the reaction mixture, for about 1 to 10 hours.

The biphenyl derivatives can be synthesized, for example, from arylboronic acid derivatives by coupling with substituted aryl halides using transition metal catalysts, in particular palladium. Corresponding reactions are described by R. B. Miller et al. (Organometallics 1984, 3, 1261) or by A. Zuzuki et al. (Synthetic Commun. 11 (7), 513 [1981]).

The sulfonylurethanes of the formula (I) can be obtained from corresponding sulfonamides of the formula (I) by reaction with chlorocarbonic acid esters in inert high-boiling solvents, such as, for example, toluene, at temperatures of about 100° C. or the boiling points of the corresponding solvents.

Sulfonyl-sulfonamides can be prepared analogously from the corresponding sulfonamides by reaction with sulfonic acid chlorides or sulfamoyl chlorides.

If necessary, the sulfonamide radical can be produced starting from an amino group, by means of a Meerwein reaction. For this, the hydrochloride of the amine is first diazotized and the diazotization product is then reacted with sulfur dioxide in glacial acetic acid in the presence of a copper catalyst. Subsequent action of ammonia leads to the sulfonamido group.

Alternatively, a corresponding thiophenol can be converted into a sulfonamide by oxidation with chlorine and subsequent action of ammonia.

Compounds which are additionally preferably employed for the treatment of disturbances in cardiac rhythm are the compounds of the formula (III), in which the symbols have the following meaning:

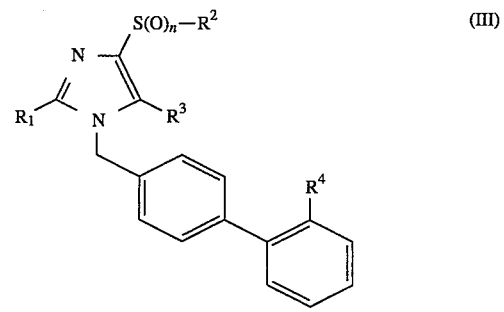

(III)

a) $R^1$ is $(C_1–C_7)$-alkyl, $(C_3–C_7)$-alkenyl or $(C_3–C_7)$-alkynyl; in particular $(C_1–C_3)$-alkyl, preferably n-propyl or ethyl, but in particular n-propyl b) $R^2$ is $(C_1–C_6)$-alkyl, preferably methyl c) $R^3$ is $—CO—R^6$ d) $R^4$ is $SO_2—NH—CO—NR^7R^9$, $SO_2—NH—COO—R^7$ or $SO_2—NH—CO—R^7$, $SO_2N=CH—N(CH_3)_2$ e) $R^6$ is hydrogen or $OR^7$ but especially hydrogen, f) $R^7$ and $R^9$ are identical or different and are hydrogen, $(C_1–C_6)$-alkyl, preferably methyl, ethyl or propyl, $(C_3–C_8)$-cycloalkyl, $(C_3–C_6)$-cycloalkyl-$(C_1–C_3)$-alkyl, $(C_6–C_{12})$-aryl, preferably phenyl or $(C_6–C_{10})$-aryl-$(C_1–C_4)$-alkyl, $(C_2–C_6)$-alkenyl, $(C_3–C_6)$-alkenoyl or $(C_3–C_6)$-alkynyl g) n is 0, 1 or 2, especially 0, and tolerated salts thereof, since these compounds are suitable in particular as therapeutic agents because of their metabolization in the human body.

The invention furthermore relates to the use of compounds of the formula (II)

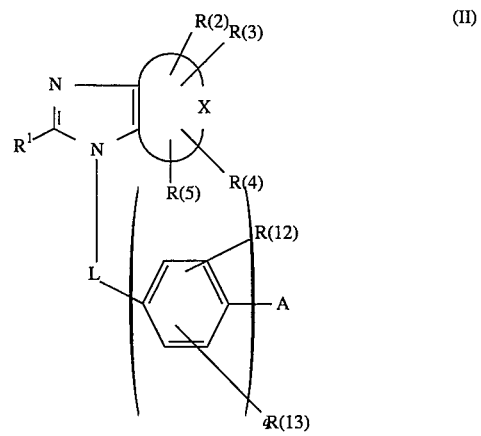

(II)

in which the symbols have the following meaning:

X is a monocyclic radical having 3, 4 or 5 ring atoms or a bicyclic radical having 8–10 ring atoms, which can be completely or partly hydrogenated and in which one or more CH or $CH_2$ groups can be replaced by N, NH or O;

R(1) is

1. $(C_1-C_{10})$-alkyl,
2. $(C_3-C_{10})$-alkenyl,
3. $(C_3-C_{10})$-alkynyl,
4. OR(6),
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkynyl,
9. $(CH_2)_m$—B—$(CH_2)_n$—R(7),
10. benzyl,
11. a radical as defined under 1., 2., 3. or 9., which is monosubstituted by $CO_2R(6)$,
12. a radical as defined under 1., 2., 3. or 9. in which 1 to all the H atoms are replaced by fluorine or
13. the radical defined under 10., which is substituted on the phenyl by 1 or 2 identical or different radicals from the series comprising halogen, $(C_1-C_4)$-alkoxy and nitro;

R(2), R(3), R(4) and R(5) are identical or different and are
1. Hydrogen, halogen, hydroxyl, cyano, nitro, sulfo, formyl, benzoyl, $(C_1-C_6)$-acyl, $(C_1-C_8)$-acyloxy, mercapto, carboxyl, $(C_1-C_4)$-alkoxycarbonyl,
2. a linear or branched, optionally substituted alkyl, alkenyl, alkoxy or alkylthio radical containing up to 6 carbon atoms,
3. an aryl, arylalkyl or arylalkenyl radical, in which the alkyl and alkenyl substituent is unbranched or branched and contains up to 6 carbon atoms and the aryl substituent is a monocyclic radical having 5 or 6 ring atoms or fused rings having 8 to 14 ring atoms, which contain one or more hetero atoms, such as O, N or S, and are optionally substituted, or
4. a radical

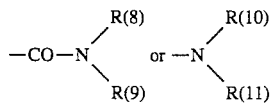

R(6) is
1. hydrogen,
2. $(C_1-C_8)$-alkyl,
3. $(C_3-C_8)$-cycloalkyl,
4. phenyl,
5. benzyl or
6. the radical defined under 2. in which 1 to all the H atoms are replaced by fluorine;

R(7) is
1. hydrogen,
2. $(C_1-C_6)$-alkyl,
3. $(C_3-C_8)$-cycloalkyl,
4. $(C_2-C_4)$-alkenyl or
5. $(C_2-C_4)$-alkynyl, R(8) and R(9) or R(10) and R(11) either are identical or different and are
1. hydrogen,
2. $(C_1-C_6)$-alkyl or $(C_1-C_6)$-alkenyl, unsubstituted or substituted by halogen, hydroxyl or $(C_{1-C6})$-alkoxy or
3. aryl or $(C_1-C_6)$-alkylaryl, in which the aryl radical is monocyclic with 5 or 6 ring atoms or bicyclic with 8–10 ring atoms, optionally contains one or more hetero atoms, such as O, N and S, and is substituted by 1 or 2 identical or different radicals from the series comprising halogen, hydroxyl, nitro, $(C_1-C_6)$-alkyl, $(C_1-C_6)$-alkenyl, $(C_1-C_4)$-alkanoyl, $(C_1-C_4)$-alkanoyloxy and $CO_2R(6)$; or R(8) and R(9) and R(11), together with the N atom carrying them, form a 4- to 8-membered ring, which is saturated or unsaturated, can contain a further hetero atom chosen from the group comprising N, O and S and is unsubstituted or substituted by halogen, hydroxyl, $(C_1-C_4)$-alkyl, $(C_1-C_4)$-alkenyl, $(C_1-C_4)$-alkyloxy and $CO_2R(6)$, or R(10) and R(11) are either identical or different and are an acyl radical having up to 6 carbon atoms or a $(C_1-C_6)$-alkyl or $(C_6-C_{12})$-aryl radical, which are optionally substituted by halogen or $(C_1-C_6)$-alkyl radicals;

L is $(C_1-C_3)$-alkanediyl, preferably methylene;

R(12) and R(13) are identical or different and are
1. hydrogen,
2. halogen,
3. nitro,
4. $(C_1-C_4)$-alkyl or
5. $(C_1-C_2)$-alkoxy;

q is zero or 1;

A is either
1. the radical of a heterocyclic compound having 5–10 ring atoms, which can be mono- or bicyclic, and of which up to 9 ring atoms are carbon atoms, and which is unsubstituted or substituted by up to 6, preferably up to 3, identical or different radicals R(14) and R(15), or
2. a biphenyl radical, which is unsubstituted or substituted by up to 4, preferably up to 2, identical or different radicals R(14) and R(15), but A is necessarily substituted by at least one radical defined under R(15) 18., 19., 28., 40. or 42 and q is zero;

R(14) is
1. halogen,
2. oxo,
3. nitroso,
4. nitro,
5. amino,
6. cyano,
7. hydroxyl,
8. $(C_1-C_6)$-alkyl,
9. $(C_1-C_4)$-alkanoyl,
10. $(C_1-C_4)$-alkanoyloxy,
11. $CO_2R(6)$,
12. methanesulfonylamino,
13. trifluoromethanesulfonylamino,
14. —CO—NH—OR(16),
15. —$SO_2$—NR(17)R(18),
16. —$CH_2$—OR(18),
17. $(C_1-C_4)$-heteroaryl-$(CH_2)_q$—, preferably 1-tetrazolyl,
18. $(C_7-C_{13})$-aroyl,
19.

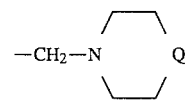

20.

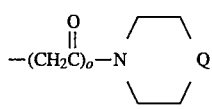

21. $(C_6-C_{12})$-aryl;

R(15) is
1. hydrogen,
2. $(C_1-C_6)$-alkyl,
3. $(C_3-C_8)$-cycloalkyl,
4. $(C_6-C_{12})$-aryl,
5. $(C_7-C_{13})$-aroyl,
6. $(C_1-C_4)$-alkoxy,
7. $(C_1-C_4)$-alkanoyloxy,
8. $(C_1-C_9)$-heteroaryl,
9. $CO_2R(6)$,
10. halogen,
11. cyano,
12. nitro,
13. NR(17)R(18),
14. hydroxyl,
15. —CO—NH—CHR(19)—$CO_2R(6)$,
16. sulfo,
17. —$SO_3R(6)$,
18. —$SO_2$—NR(18)—CO—NR(17)R(16), —$SO_2$—NR(18)—CO—OR(17), —$SO_2N(CO-O-R(17))_2$ or —$SO_2$—NR(18)—CS—NR(17)R(16),
19. —NR(18)—SO—NR(17)—$SO_2$—$CH_2$—R(18),
20. —$C(CF_3)_2OH$,
21. phosphonooxy,
22. —$PO_3H_2$,
23. —NH—$PO(OH)_2$,
24. —$S(O)_rR(17)$,
25. —CO—R(20),
26. —CO—NR(17)R(16),
27.

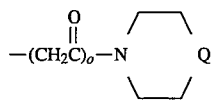

28.

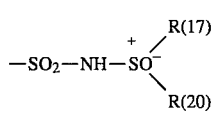

29.

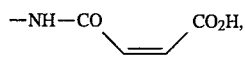

30.

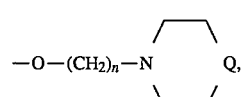

31. 5-tetrazolyl-NH—CO—,
32. —CO—NH—NH—$SO_2CF_3$,
33.

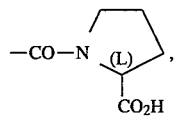

34.

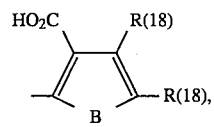

35.

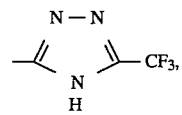

36.

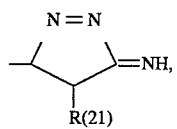

37.

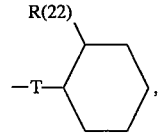

38.

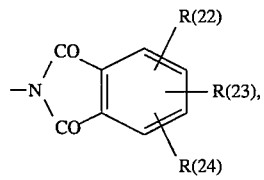

39. —CO—NH—$SO_2$—R(6),
40. —$SO_2$—NH—CO—R(17),
41. the radical defined under 4., substituted by one or two identical or different radicals from the series comprising halogen, cyano, nitro, NR(17)R(18) and hydroxyl, or
42. R(15), together with R(14), is —CO—NH—$SO_2$—;

R(16) and R(17) are identical or different and are
1. hydrogen,
2. $(C_1-C_6)$-alkyl,
3. $(C_3-C_8)$-cycloalkyl,
4. $(C_6-C_{12})$-aryl, preferably phenyl,
5. $(C_6-C_{10})$-aryl-$(C_1-C_4)$-alkyl, 6. $(C_1-C_9)$-heteroaryl, which can be partly or completely hydrogenated, preferably 2-pyrimidinyl, 1-piperidinyl or quinuclidinyl,
7. $(C_3-C_6)$-alkenoyl,
8. a radical as defined under 4., 5., 6., 9., 14., 15., 16., 18., 19., or 20., substituted by 1 or 2 identical or different radicals from the series comprising hydroxyl, methoxy, nitro, cyano, $CO_2R(6)$, trifluoromethyl, —NR(25)R(26) and

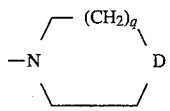

9. $(C_1-C_9)$-heteroaryl-$(C_1-C_3)$-alkyl, in which the heteroaryl part can be partly or completely hydrogenated,
10. the radical defined under 2. in which 1 to all the H atoms are replaced by fluorine,
11. $(C_2-C_6)$-alkenyl,
12. $(C_3-C_8)$-cycloalkenyl,
13. $(C_3-C_8)$-cycloalkenyl-$(C_1-C_3)$-alkyl,
14. $(C_3-C_8)$-cycloalkyl-$(C_1-C_4)$-alkyl,
15. $(C_6-C_{10})$-aryl-$(C_3-C_6)$-alkenyl,
16. $(C_1-C_9)$-hetaryl-$(C_3-C_6)$-alkenyl,
17. $(C_3-C_6)$-alkynyl,
18. $(C_6-C_{10})$-aryl-$(C_3-C_6)$-alkynyl,
19. $(C_1-C_9)$-hetaryl-$(C_3-C_6)$-alkynyl,
20. a radical of the formula

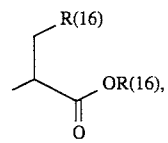

in which R(16) cannot have the meaning of 20., or
21. R(16) and R(17), together with the N atom carrying them, form a hetaryl, which can also be partly or completely hydrogenated;

R(18) is
1. hydrogen,
2. $(C_1-C_6)$-alkyl,
3. $(C_3-C_8)$-cycloalkyl,
4. $(C_6-C_{12})$-aryl-$(C_1-C_6)$-alkyl, preferably benzyl,
5. phenyl or
6. $(C_1-C_9)$-heteroaryl;

R(19) is
1. hydrogen,
2. $(C_1-C_6)$-alkyl,
3. $(C_3-C_8)$-cycloalkyl,
4. phenyl or
5. benzyl R(20) is
1. hydrogen,
2. $(C_1-C_6)$-alkyl,
3. $(C_3-C_8)$-cycloalkyl,
4. phenyl-$(CH_2)_q$—,
5. OR(19),
6. NR(25)R(26) or

7.

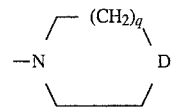

R(21) is cyano, nitro or $CO_2R(18)$;
R(22) is $CO_2R(6)$ or $CH_2CO_2R(6)$;
R(23) is hydrogen, halogen, $(C_1-C_4)$-alkyl or $(C_1-C_4)$-alkoxy;
R(24) is hydrogen, $(C_1-C_4)$-alkyl or phenyl;
R(25) and R(26) are identical or different and are
1. hydrogen,
2. $(C_1-C_4)$-alkyl,
3. phenyl,
4. benzyl or
5. α-methylbenzyl;

D is NR(23), O or $CH_2$;
B is O, NR(18) or S;
T is
1. a single bond,
2. —CO—,
3. —$CH_2$—,
4. —O—,
5. —S—,
6. —NR(28)—,
7. —CO—NR(28)—,
8. —NR(28)—CO—,
9. —O—$CH_2$—,
10. —$CH_2$—O—,
11. —S—$CH_2$—,
12. —$CH_2$—S—,
13. —NH—CR(27)R(29)—,
14. —NR(28)—$SO_2$—,
15. —CR(27)R(29)—NH—,
16. —CR(27)R(29)—NH—,
17. —CH=CH—,
18. —CF=CF—,
19. —CH=CF—,
20. —CF=CH—,
21. —$CH_2$—$CH_2$—,
22. —$CF_2$—$CF_2$—,
23. —CH(OR(6))—,
24. —CH(OCOR(19))—,
25.

or
26.

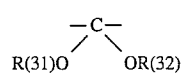

R(27) and R(29) are identical or different and are hydrogen, $(C_1-C_5)$-alkyl, phenyl, allyl or benzyl;
R(28) is hydrogen, $(C_1-C_6)$-alkyl, benzyl or allyl;
R(30) is
1. NR(27)R(28),
2. ureido, 3. thioureido,
4. toluene-4-sulfonyl or
5. benzenesulfonylamino;

R(31) and R(32) are identical or different and are $(C_1-C_4)$-alkyl, or together are $-(CH_2)_q-$;

Q is $CH_2$, NH, O or S;

n is an integer from 1 to 5;

m is an integer from 0 to 3;

o is an integer from 1 to 10; and r is zero, 1 or 2, and physiologically tolerated salts thereof.

Alkyl, alkenyl and alkynyl can be straight-chain or branched. The same applies to radicals derived therefrom, such as alkanoyl or alkoxy.

Cycloalkyl is also understood as meaning alkyl-substituted rings.

$(C_6-C_{12})$-Aryl is, for example, phenyl, naphthyl or biphenylyl, preferably phenyl. The same applies to radicals derived therefrom, such as aroyl or aralkyl.

$(C_1-C_9)$-Heteroaryl is understood as meaning, in particular, radicals which are derived from phenyl or naphthyl, in which one or more CH groups are replaced by N and/or in which at least two adjacent CH groups are replaced by S, NH or O (to form a five-membered aromatic ring). Furthermore, 1 or both atoms of the condensation site of bicyclic radicals (such as in indolizinyl) can also be an N atom.

These are, for example, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

The fused heterobicyclic compound AH from which the radical A is derived is understood as meaning, in particular, a bicyclic ring system having 8 to 10 ring atoms, up to 9 ring atoms of which are carbon atoms, and in which two adjacent atoms are common constituents of the two rings. One or both of these rings are derived formally from benzene, in which one or more CH groups are replaced by N, $O^+$ and $S^+$ and/or in which two adjacent CH groups are replaced by S, NH or O (to form a five-membered aromatic ring).

A is, for example, a radical of benzothiophene, benzofuran, indole, isoindole, indazole, benzimidazole, quinoline, isoquinoline, phthalazine, quinoxaline, quinazoline, cinnoline, benzothiazole, benzothiazole 1,1-dioxide, coumarin, chroman, benzoxazole, benzisothiazole, benzodiazine, benzotriazole, benzotriazine, benzoxazine, imidazopyridine, imidazo-pyrimidine, imidazo-pyrazine, imidazo-pyridazine, imidazo-thiazole, pyrazolopyridine, thienopyridine and pyrrolopyrimidine. The heterobicyclic compound AH mentioned can also be partly or completely hydrogenated. Preferably, however, one ring of AH remains aromatic, a benzofused heterobicyclic compound AH being particularly preferred.

In the case of S-containing and/or partly saturated radicals the bicyclic radical can also be oxo-substituted, for example, as is the case in the radical of benzo- 1,2,3-triazinone.

A is linked to the group

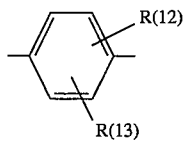

from the isocyclic or from the heterocyclic part via an alkanediyl bridge L if q is zero and via a single bond if q is 1.

An iso- or heterocyclic compound $XH_2$ from which the mono- or bicyclic radical X is derived is understood as meaning, for example, a radical of cyclopentane, cyclohexane, cycloheptane, cyclopentene, cyclohexene, cycloheptene, benzene, naphthalene, furan, thiophene, pyrrole, pyridine, pyridazine, pyrimidine, piperidine, piperazine, morpholine, indole, indazole, oxazole, isoaxazole, quinoline, isoquinoline, benzothiophene, benzofuran, benzothiazole, benzoxazole, imidazopyridine, imidazopyrimidine and rufopyridine.

Halogen is fluorine, chlorine, bromine and iodine. Physiologically tolerated salts of compounds of the formula (II) are understood as meaning both organic and inorganic salts thereof, such as are described in Remington's Pharmaceutical Sciences, 17th Edition, page 1418 (1985). Because of their physical and chemical stability and solubility, the sodium, potassium, calcium and ammonium salts, inter alia, are preferred for acid groups, and salts with hydrochloric acid, sulfuric acid, phosphoric acid, carboxylic acids or sulfonic acids, such as acetic acid, citric acid, benzoic acid, maleic acid, fumaric acid, tartaric acid and p-toluenesulfonic acid, inter alia, are preferred for basic groups.

Compounds which are preferably employed against the disorders mentioned are those of the formula (IV)

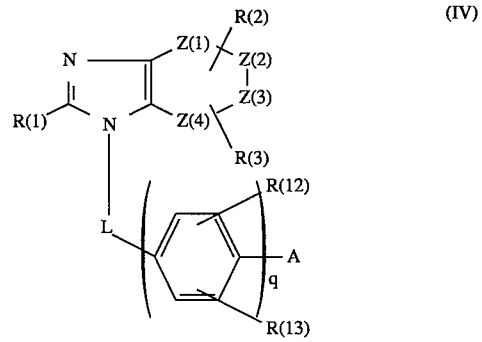

where the symbols have the following meaning:

Z(1), Z(2), Z(3) and Z(4) are
1. $-CH-$,
2. $-CH=$ or
3. a radical defined under 2. in which 1 or 2 methine groups are replaced by nitrogen; preferably, Z(4) is N, R(1) is
1. $(C_1-C_{10})$-alkyl,
2. $(C_3-C_{10})$-alkenyl,
3. $(C_3-C_{10})$-alkynyl,
4. $(C_3-C_8)$-cycloalkyl,
5. benzyl or
6. benzyl which is substituted as described above;

R(2) and R(3) are identical or different and are
1. hydrogen,
2. hydroxyl,
3. halogen,
4. a linear or branched $(C_1-C_6)$-alkyl radical, unsubstituted or substituted by one or more identical or different substituents from the series comprising halogen, hydroxyl, $(C_1-C_4)$-alkoxy, $(C_1-C_4)$-alkylthio and mercapto or
5. $-CO_2R(6)$;

T is a single bond, $-O-$, $-CO-$, $-NHCO-$ or $-OCH_2-$, and the other radicals and variables are as defined above.

Particularly preferred compounds of the formula (IV) are those in which

R(1) is $(C_1-C_7)$-alkyl, $(C_3-C_7)$-alkenyl or $(C_3-C_7)$-alkynyl;

R(6) is hydrogen or $(C_1-C_4)$-alkyl;

R(12) and R(13) are identical or different and are hydrogen or $(C_1-C_4)$-alkyl;

(R14) is
1. $(C_1-C_4)$-alkyl,
2. $(C_1-C_4)$-alkoxy,
3. cyano,
4. amino,
5. nitro,
6. fluorine, chlorine or bromine,
7. $(C_1-C_4)$-heteroaryl—$CH_2$,
8. $(C_1-C_4)$-alkanoyloxy,
9. $(C_1-C_4)$-alkanoyl,
10. benzoyl or
11. tetrazolyl;

R (15) is
1. $(C_1-C_4)$-alkyl,
2. $(C_6-C_{12})$-aryl,
3. $(C_1-C_3)$-alkanoyloxy,
4. $(C_1-C_4)$-alkoxy,
5. $(C_1-C_9)$-heteroaryl, preferably 5-tetrazolyl,
6. cyano,
7. nitro,
8. hydroxyl,
9. $SO_3R(6)$,
10. chlorine, bromine,
11. $CO_2R(6)$,
12. CO—NH—R(19),
13. CO—R(20),
14. $SO_2$—NR(18)—CO—NR(17)R(16),
15. $SO_2$—NR(18)—CO—O—R(17) or $SO_2N(CO-OR(17))_2$,
16. CO—CHR (19)-$CO_2H$,
17. $(C_1-C_4)$-alkyl-$CO_2H$,
18. NH—CO—NH—$SO_2$—$CH_2$—R(19),
20.

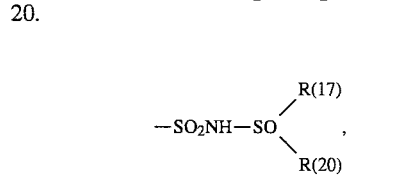

21.

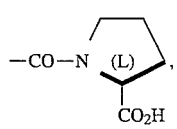

22.

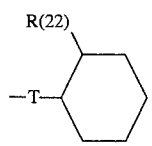

23. (R14), together with R(15), is —CO—NH—$SO_2$;

L is —$CH_2$—;

R(18) is hydrogen; and

R(25) and R(26) independently of one another are hydrogen or $(C_1-C_4)$-alkyl, and physiologically tolerated salts thereof.

The process for the preparation of compounds of the formula (II) comprises alkylating compounds of the formula (IIIb)

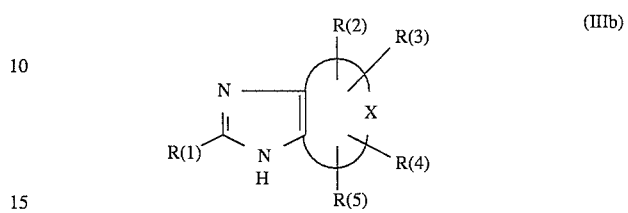

in which R(1), R(2), R(3), R(4), R(5) and X are as defined above, with compounds of the formula (IVb)

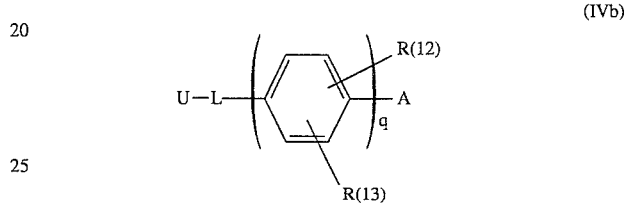

in which L, q, R(12), R(13) and A are as defined above and U is a leaving group, splitting off again any protective groups temporarily introduced, and if appropriate converting the resulting compounds of the formula (II) into their physiologically tolerated salts.

Suitable leaving groups U are preferably nucleofugic groups (cf. Angew. Chem. 72 (1960) ), such as halogen, o-toluenesulfonate, mesylate or triflate.

Processes for the preparation of the precursors of the formula (IIIb) are known, inter alia, from U.S. Pat. No. 4,880,804, DE 3 911 603, EP-A-399 731, EP-A-399 732, EP-A-400 835, EP-A-400 974, EP-A-415 886, EP-A-420 237, EP-A-425 921 and EP-A-434 038.

Corresponding benzyl halides, tosylates, mesylates or triflates or corresponding alkyl halides, tosylates, mesylates or triflates, for example, are suitable for alkylation of the compounds of the formula (IIIb).

These compounds are prepared in a manner which is known per se, for example by halogenation of the corresponding methyl precursors. N-bromosuccinimide is preferably employed for this, cf., for example, J. Org. Chem. 44, 4733 (1979) and Helv. Chim. Acta 62, 2661 (1979).

The benzimidazole, benzothiophene, imidazo-pyridine and imidazo-pyrimidine derivatives having a $CH_3$ group on the nucleus are synthesized, inter alia, by the method of R. P. Dickson et al. in J. Med. Chem. 29, 1937 (1986), E. Abignente et al. in J. Heterocyclic Chem. 26, 1875 (1989), A. Koubsack et al. in J. Org. Chem. 41, 3399 (1976) and by the method of F. Santer et al. in Mh. Chem. 99, 715 (1968).

The biphenyl derivatives can be synthesized, for example, starting from arylboronic acid derivatives by coupling with substituted aryl halides using transition metal catalysts, in particular palladium. Corresponding reactions are described by R. B. Miller et al. (Organometallics 1984, 3, 1261) or by A. Zuzuki et al. (Synthetic Commun. 11 (7), 513 (1981)).

The sulfonylurethane derivatives of the formula (II) can be obtained from corresponding sulfonamides of the formula (II) by reaction with chlorocarbonic acid esters or by reaction with dimethyl dicarbonate and bases, such as, for example, potassium carbonate, in inert solvents at temperatures up to the boiling point of the corresponding solvent.

The sulfonylurea derivatives of the formula (II) can be prepared either from the corresponding sulfonamides of the formula (II) by reaction with isocyanates or with 2,2,2-trichloroacetamide derivatives of a suitable amine in inert high-boiling solvents, such as, for example, dimethyl sulfoxide, or from sulfonylurethanes of the formula (II) by the action of the corresponding amine in an inert high-boiling solvent, such as, for example, toluene, at temperatures up to the boiling point of the particular solvent.

If necessary, the sulfonamide radical can be produced starting from an amino group by means of a Meerwein rearrangement. For this, the hydrochloride of the amine is first diazotized and the diazotization product is then reacted with sulfur dioxide in glacial acetic acid in the presence of a copper catalyst. The subsequent action of ammonia leads to the sulfonamide group. The alkylation is carried out in a manner analogous to processes which are known in principle.

The imidazo-fused derivatives of the formula (IIIb) are metallized, for example in the presence of a base. Preferred bases are metal hydrides of the formula MH, such as lithium hydride, sodium hydride or potassium hydride, in, for example, dimethylformamide or dimethyl sulfoxide as the solvent, or metal alkoxides of the formula MOR, in which R is methyl, ethyl or t-butyl, the reaction being carried out in the corresponding alcohol, dimethylformamide or dimethyl sulfoxide. The salts thus formed of the imidazo derivatives are dissolved in an aprotic solvent, such as dimethylformamide or dimethyl sulfoxide, and a suitable amount of alkylating reagent is added.

An alternative possibility for deprotonation of the imdazole derivatives is, for example, reaction with potassium carbonate in dimethylformamide or dimethyl sulfoxide.

The reactions are carried out at temperatures below room temperature up to the boiling point of the reaction mixture, preferably between +20° C. and the boiling point of the reaction mixture, for a period of about 1 to 10 hours.

Of the compounds of the general formulae (I), (II), (III) and (IV), those compounds which contain, as substituents of the biphenyl system, a sulfonylurea grouping, such as, for example, —SO₂—NR⁷—CO—NR⁶R⁹, have proven to be particularly advantageous in respect of their metabolism, in particular in humans.

The following compounds are also of particular interest in respect of their therapeutic action in the treatment of coronary heart disease and the other disorders mentioned:

1. ethyl 2-n-butyl-1-[(2'-n-propylaminocarbonylaminosulfonyl-biphenyl- 4-yl)methyl]-4-methylthio-imidazole-5-carboxylate
2. -n-butyl-1-[(2'-n-propylaminocarbonylaminosulfonyl-biphenyl- 4-yl)methyl]-4-methylthio-imidazole-5-carboxylic acid
3. ethyl 2-n-propyl-1-[(2'-n-propylaminocarbonylaminosulfonyl-biphenyl- 4-yl)methyl]-4-methylthio-imidazole-5-carboxylate
4. 2-n-propyl-1-[(2'-n-propylaminocarbonylaminosulfonyl-biphenyl- 4-yl)methyl]-4-methylthio-imidazole-5-carboxylic acid
5. 3-[(2'-allylaminocarbonylaminosulfonyl-biphenyl-4-yl)methyl]-2-ethyl-7-methyl-imidazo[4,5-b]pyridine
6. 5,7-dimethyl-3-[(2'-methoxycarbonylaminosulfonyl-biphenyl- 4-yl)methyl]-2-ethyl-imidazol[4,5-b]pyridine
7. the potassium salt of 2-n-butyl-4-chloro-5-hydroxymethyl- 1-[(2'-(1H-tetrazol-5-yl)-biphenyl-4-yl)-methyl]-imidazole, known from EP-A 324 377
8. 5,7-dimethyl-3-[(2'-tetrazolyl-biphenyl-4yl)-methyl]-imidazo[4,5-b]pyridine, known from EP-A 399 731, EP-A 400 974 and N. B. Mantlo, J. Med. Chem. 34, 1991, 2919–2922
9. 2-n-butyl-4-chloro-1-[(2'-(1H-tetrazol-5-yl)-biphenyl-4-yl)-methyl]-imidazol-5-carboxylic acid (cf. P. C. Wong et al., J. Pharmacol. Exp. Ther. 252, 711–718, 1990)

and physiologically tolerated salts thereof, such as the corresponding mono- and dipotassium salts.

Furthermore, treatment of coronary heart disease and the other disorders mentioned is also possible using angiotensin II receptor antagonists of the general formulae VI–XX, which are described in the particular prior art stated.

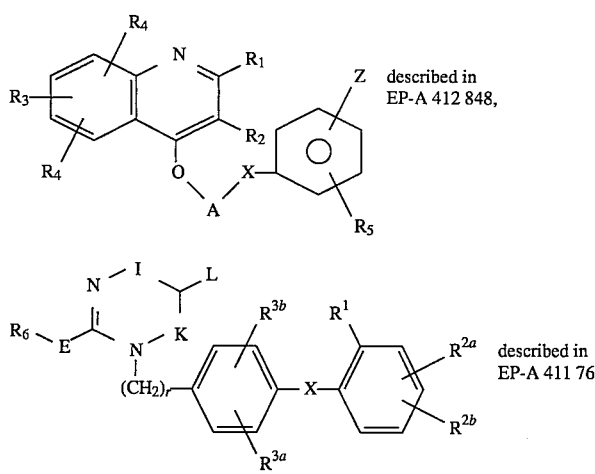

(VI) described in EP-A 412 848, (VII) described in EP-A 411 766,

-continued
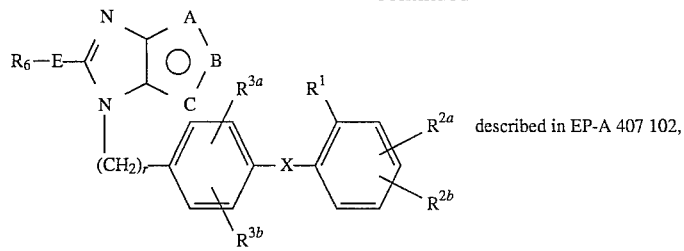 described in EP-A 407 102, (VIII)
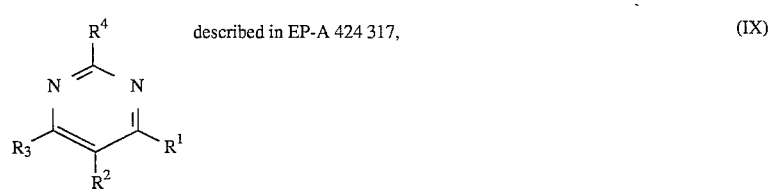 described in EP-A 424 317, (IX)
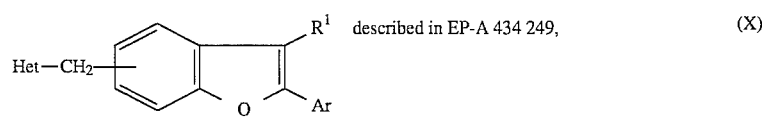 described in EP-A 434 249, (X)
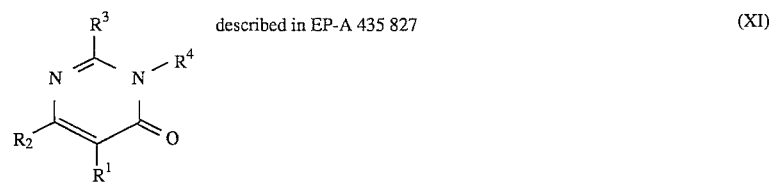 described in EP-A 435 827 (XI)
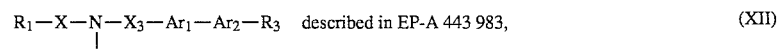 described in EP-A 443 983, (XII)
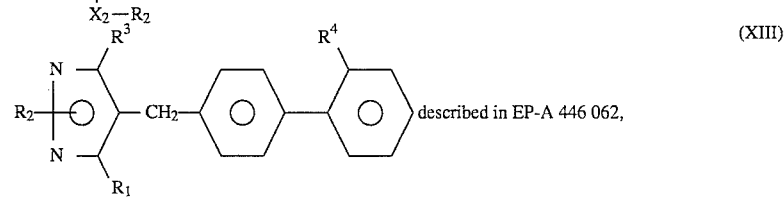 described in EP-A 446 062, (XIII)
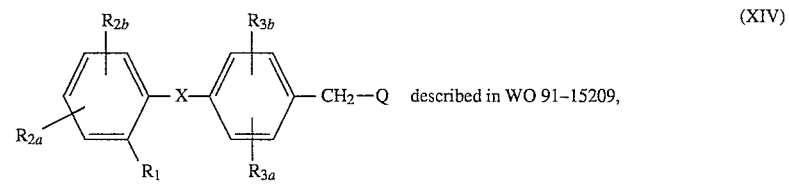 described in WO 91–15209, (XIV)
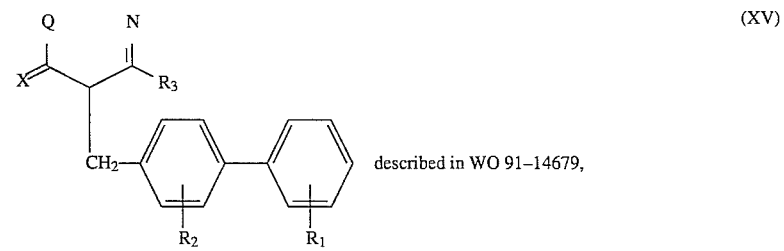 described in WO 91–14679, (XV)
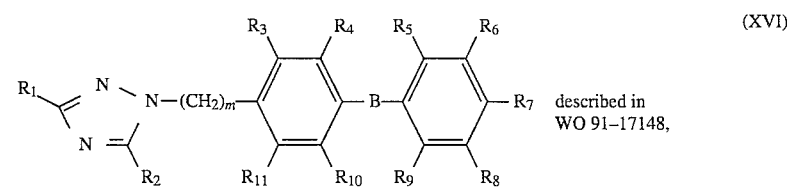 described in WO 91–17148, (XVI)

-continued

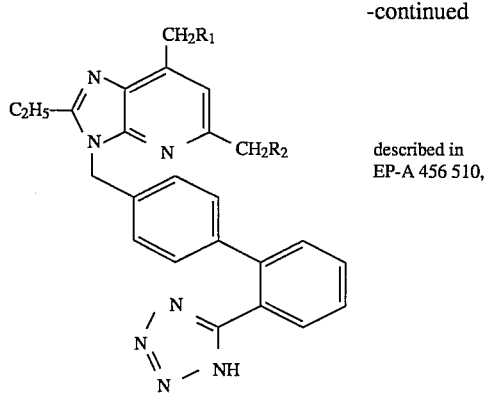
described in EP-A 456 510, (XVII)

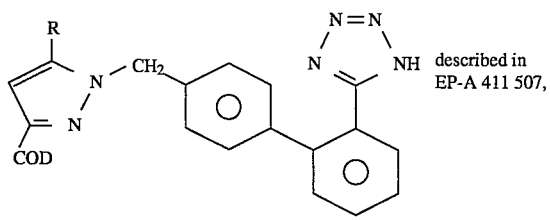
described in EP-A 411 507, (XVIII)

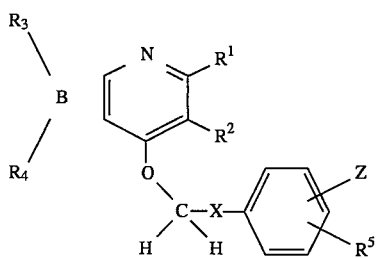 (XIX)

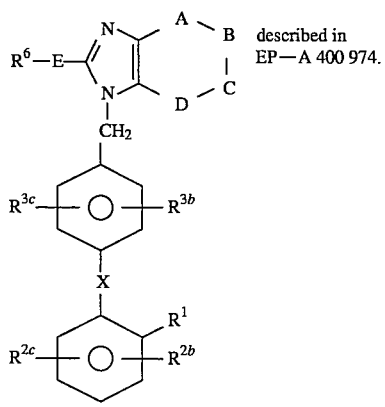
described in EP—A 400 974. (XX)

In carrying out the method according to the invention, the angiotensin II receptor antagonists described above can be used on mammals, such as monkeys, dogs, cats or rats, but especially in humans.

The compounds suitable for the use according to the invention are advantageously incorporated into pharmaceutical preparations in the customary manner. They can be brought into the customary administration forms, such as capsules, tablets, coated tablets, solutions, ointments and emulsions, and also into depot form. If appropriate, the active compound can also be present in microencapsulated form. The preparations can contain physiologically tolerated organic or inorganic auxiliaries or additives, for example granulating substances, adhesives and binders, lubricants, suspending agents, solvents, antibacterial agents, wetting agents and preservatives.

The treatment according to the invention can be effected either via the mucosae or parenterally. Oral and parenteral (such as i.v. or i.m.) use forms are preferred.

For an oral use form, the active compounds are mixed with the additives customary for this purpose, such as excipients, stabilizers or inert diluents, and the mixtures brought into suitable presentation forms, such as tablets, coated tablets, had gelatin capsules, aqueous, alcoholic or oily suspensions or aqueous, alcoholic or oily solutions, by customary methods. Inert excipients which can be used are, for example, gum arabic, magnesium carbonate, potassium phosphate, lactose, glucose or starch, in particular maize starch. The compounds can be formulated as either dry or moist granules. Possible oily excipients or solvents are, for example, vegetable and animal oils, such as sunflower oil or cod-liver oil.

For subcutaneous or intravenous administration, the active compounds, or physiologically tolerated salts thereof, are converted into solution form, into suspensions or emulsions, if desired with the substances customary for this purpose, such as solubilizing agents, an emulsifier or other auxiliaries. Possible solvents for the active combinations and the corresponding physiologically tolerated salts are, for example: water, physiological saline solutions or alcohols, for example ethanol, propanediol or glycerol, and in addition also sugar solutions, such as glucose solutions or mannitol solutions, or also a mixture of the various solvents mentioned.

The compounds described are preferably administered in doses of 0.1 to 100 mg/kg, specifically preferably 0.1 to 50 mg, in particular 1 to 30 mg, being administered once to three times daily.

The efficacy of the compounds described for the treatment and prophylaxis of coronary heart disease, of septic shock, of cognitive and erectile dysfunction, and renal and immunological disorders can be deduced from the experiment on the in vitro formation of cGMP on endothelial cells of the bovine aorta.

EXAMPLE 1

The following investigation was carried out with 2-n-butyl- 4-chloro-1-[(2'-(1H-tetrazol-5-yl )biphenyl-4-yl)methyl] imidazole-5-carboxylic acid (T):

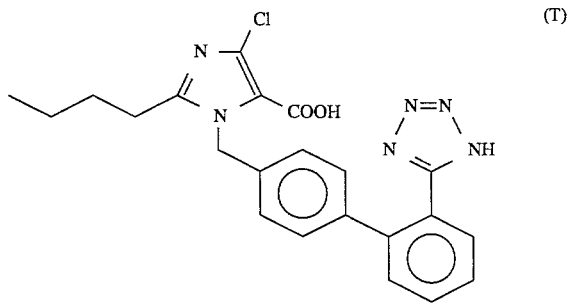
(T)

Experiment

Effect of angiotensin II on endothelial cells of the bovine aorta with preincubation with the $AT_1$ receptor antagonist 2-n-butyl-4-chloro-1-[(2'-(1H-tetrazol-5-yl)biphenyl- 4-yl-)methyl]imidazole-5-carboxylic acid.

Method

Primary cultivated endothelial cells of the bovine aorta are incubated with $10^{-7}$–$10^{-4}$ mol/l angiotensin II (ANG II) for 3 minutes, and the changes in cyclic GMP (cGMP) concentration are determined in pmol/mg of protein by a radioimmunoassay (see curve A in FIG. 1).

Measurement is repeated after preincubation (5 minutes) of the endothelial cells with a) a stereospecific inhibitor of NO synthesis ($N^{\omega}$-nitro-L-arginine L-NNA ($10^{-5}$ mol/l ) ), (see curve B in FIG. 1 )

b) a specific bradykinin antagonist, the decapeptide (HOE 140) H-D-Arg-Arg-Pro-Hyp-Gly-Thi-Ser-D-Tic-Oic-Arg-OH (see Hock et al., Br. J. Pharmacol. 102 (1991) 769–773 and Wirth et al., Br. J. Pharmacol. 102 (1991) 774–777) ($10^{-7}$ mol/l ) ), (see curve C in FIG. 1 )

c ) the $AT_2$-receptor-specific angiotensin II receptor antagonist PD 123 177 ($10^{-5}$ mol/l ) (disclosed in J. Med. Chem. 1991, 34, 3248–3260) (see curve E in FIG. 1)

d) and the $AT_1$-specific angiotensin II receptor antagonist of the formula (T) in a concentration of $10^{-5}$ mol/l (see curve D in FIG. 1 ).

The results of this experiment are shown in FIG. 1.

It follows from these measurements that the formation, stimulated by angiotensin II, of cyclic GMP (cGMP ) on endothelial cells is mediated via the $AT_2$ receptor subtype of the angiotensin II receptors.

An increased production of cyclic GMP is, however, associated with an increased endothelial nitric oxide (NO) formation (see, for example, Moncada et al., Pharmacological reviews 43, No. 2 (1991) 109–142). Selective inhibition of the $AT_1$ subtype of angiotensin II receptors with the described compounds inevitably increases, both due to the $AT_1$ receptor blockade itself and due to the compensatory renal secretion of renin correlated thereto, the amount of angiotensin II binding to the $AT_2$ receptor subtype (according to B. Bankenburg et al., Hypertension 18 (1991) 278–289 the plasma concentration of renin and angiotensin II increases by a factor of 7 and 10 respectively after treatment of SHR (spontaneously hypertensive rats) for example with the compound 2-n-butyl-4-chloro-5-hydroxymethyl-1-[(2'-(1H-tetrazol- 5-yl)biphenyl-4-yl)methyl]imidazole potassium salt in a dose of 10 mg/kg/day for 7 days; negative feedback).

The angiotensin II levels raised in this way stimulate endothelial production of cGMP and NO, which means that in principle all disorders which can be beneficially influenced by increasing the NO level become treatable. These include the coronary heart disease described at the outset.

EXAMPLE 2

The following experiment was carried out with 2-n-propyl- 1-[(2 '-n-propylaminocarbonylaminosulfonylbiphenyl-4-yl)methyl] -4-methylthioimidazole-5-carboxylic acid (U):

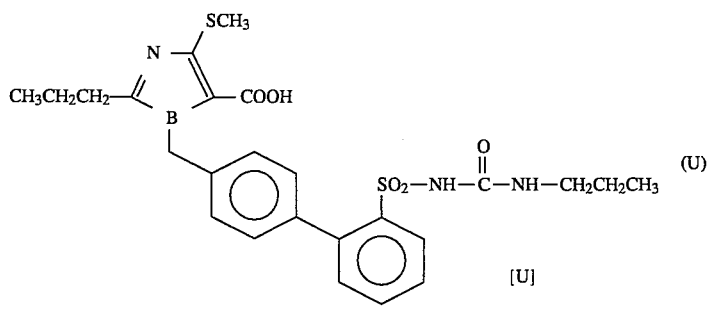

Experiment

Effect of the $AT_1$ receptor antagonist (U) on endothelial cells of the bovine aorta with preincubation with angiotensin in II.

Method

Primary cultivated endothelial cells of the bovine aorta are incubated with $10^{-4}$ mol/l angiotensin II for 3 minutes. The changes in the concentration of cyclic GMP (cGMP, cyclic guanosine monophosphate) are determined using a radioimmunoassay. The stimulatory effect of angiotensin II is taken as the 100% value. The measurement is repeated as shown in FIG. 2 after preincubation (5 minutes) of the endothelial cells with increasing concentrations from $10^{-8}$ to $10^{-4}$ mol/l of the $AT_2$-specific receptor antagonist PD 123 177 (curve A) and with increasing concentrations from $10^{-8}$ to $10^{-4}$ mol/l of the $AT_1$-selective angiotensin II receptor antagonist of the formula (U) (curve B in FIG. 2).

Figure 2:
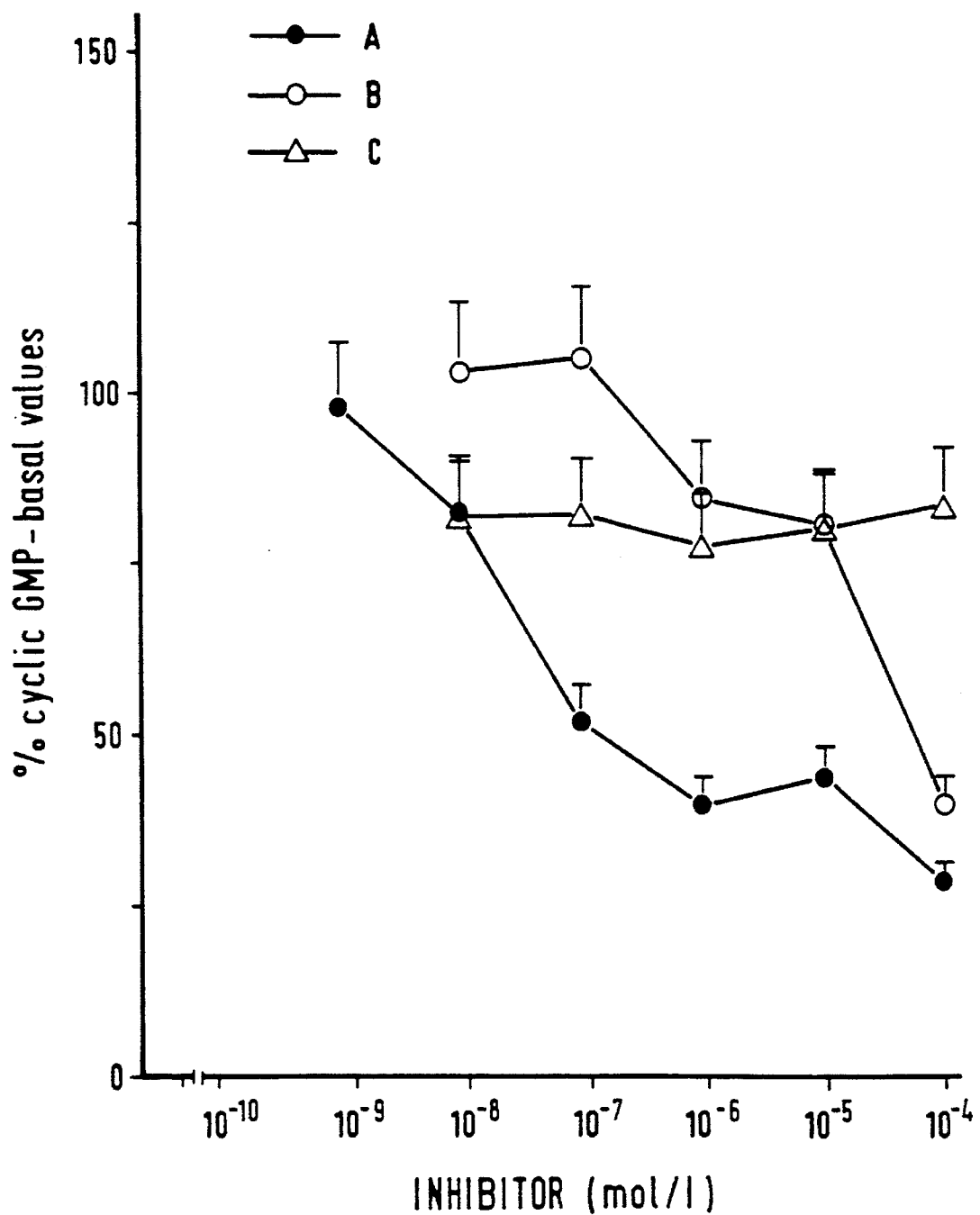
FIG. 2 depicts the effects of $AT_1$ receptor antagonists 2-n-propyl- 1-[(2'-n-propylaminocarbonylaminosulfonylbiphenyl-4-yl)methyl[-4-methylthioimidazole-5-carboxylic acid (B) and 3-[(2'allylaminocarbonylaminosulfonylbiphenyl-4-yl)methyl]-2-ethyl-7-methylimidazol[4,5-b]pyridine (C) on endothelial cells of the bovine aorta with preincubation with angiotensin II (A).

The result of the experiment is shown in FIG. 2.

EXAMPLE 3

The following experiment was carried out with the imidazopyridine (V):

3-[(2'-Allylaminocarbonylaminosulfonylbiphenyl-4-yl)-methyl]-2-ethyl-7-methylimidazo[4,5-b]pyridine

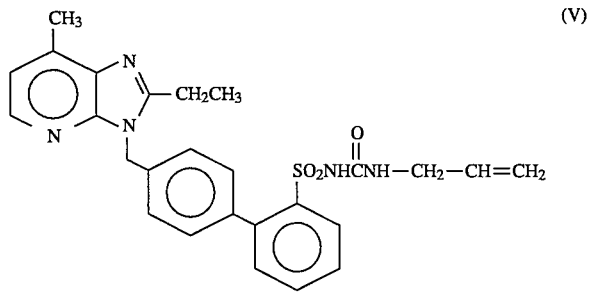

Experiment

Effect of the $AT_1$ receptor antagonist (V) on endothelial cells of the bovine aorta with preincubation with angiotensin in II.

Method

Primary cultivated endothelial cells of the bovine aorta are incubated with $10^{-4}$ mol/l angiotensin II for 3 minutes. The changes in the concentration of cyclic GMP (cGMP, cyclic guanosine monophosphate) are determined using a radioimmunoassay. The stimulatory effect of angiotensin II is taken as the 100% value. The measurement is repeated after preincubation (5 minutes) of the endothelial cells with increasing concentrations from $10^{-8}$ to $10^{-4}$ mol/l of the AT2-specific receptor antagonist PD 123 177 (see curve A) and with increasing concentrations from $10^{-8}$ to $10^{-4}$ mol/l of the $AT_1$-selective angiotensin II receptor antagonist of the formula (V) (see curve C). The result of the experiment is shown in FIG. 2.

The following examples indicate the forms to be used for treating the said disorders by the method according to the invention. The compounds of the formulae I–IV, but also the compounds VI to XX, can be converted into the corresponding forms to be used in analogy to the examples and employed for the therapy of disorders which can be influenced by NO.

EXAMPLE 4

Preparation of an agent for oral use:

1000 tablets, each of which comprises 20 mg of 2-n-propyl- 1-[(2'-n-propylaminocarbonylaminosulfonylbiphenyl- 4-yl)methyl]-4-methylthio-imidazole-5-carboxylic acid, are prepared using the following auxiliaries.

| | |
|---|---|
| 2-n-Propyl-1-[(2'-n-propylaminocarbonyl-aminosulfonyl-biphenyl-4-yl)methyl]-4-methylthio-imidazole-5-carboxylic acid | 20.0 g |
| Corn starch | 140.0 g |
| Gelatin | 7.5 g |
| Microcrystalline cellulose | 2.5 g |
| Magnesium stearate | 2.5 g |

The 2-n-propyl-1-[(2'-n-propylaminocarbonylaminosulfonyl-biphenyl- 4-yl)methyl]-4-methylthio-imidazole-5carboxylic acid and corn starch are mixed with an aqueous gelatin solution. The mixture is dried and ground to granules. The microcrystalline cellulose and magnesium stearate are mixed with the granules. The resulting granules are pressed to 1000 tablets, each tablet comprising 20 mg of the angiotensin II receptor antagonist.

Tablets which, in place of the abovementioned active compound (U), contain the active compound (T) mentioned in Example 1 or the active compound (V) mentioned in Example 3 are prepared analogously.

EXAMPLE 5

Analogously to Example 4, 1000 tablets, each of which contains 3 mg of 2-n-propyl-1-[(2'-n-propylaminocarbonylaminosulfonyl-biphenyl- 4-yl)methyl]-4-methylthioimidazole- 5-carboxylic acid, are prepared by using 3 g of this compound in the mixture described in Example 4.

EXAMPLE 6

Gelatin capsules, each of which contains 20 mg of 2-n-propyl- 1-[(2'-n-propylaminocarbonylaminosulfonyl-biphenyl- 4-yl)methyl]-4-methylthio-imidazole-5-carboxylic acid, are filled with the following mixture:

| 2-n-Propyl-1-[(2'-n-propylaminocarbonyl-aminosulfonyl-biphenyl-4-yl)methyl]-4-methylthio-imidazole-5-carboxylic acid | 20 mg |
|---|---|
| Potassium stearate | 1 mg |
| Lactose | 214 mg |

Gelatin capsules with the active compounds (T) and (V) are prepared analogously.

EXAMPLE 7

Analogously to Example 6, capsules, each of which contains 3 mg of 2-n-Propyl-1-[(2'-n-propylaminocarbonylaminosulfonyl-biphenyl- 4-yl)methyl]-4-methylthio-imidazole- 5-carboxylic acid, are prepared using 3 mg of active compound.

EXAMPLE 8

The preparation of an injection solution for the treatment of inter alia coronary heart disease is described below:

| 2-n-Propyl-1-[(2'-n-propylaminocarbonyl-aminosulfonyl-biphenyl-4-yl)methyl]-4-methylthio-imidazole-5-carboxylic acid | 1 g |
|---|---|
| Methylparaben | 5 g |
| Propylparaben | 1 g |
| Sodium chloride | 25 g |
| Water for injections | 5 l |

The 2-n-propyl-1-[(2'-n-propylaminocarbonylaminosulfonylbiphenyl- 4-yl)methyl]-4-methylthio-imidazole-5-carboxylic acid, the preservatives and the sodium chloride are dissolved in 3 l of water for injections and the solution is made up to 5 l with water for injections. The solution is subjected to sterile filtration and introduced aseptically into presterilized bottles, which are closed with sterilized rubber caps. Each bottle contains 5 ml of solution.

Injection solutions which contain the active compounds (T) or (V) are prepared analogously.

EXAMPLE 9

Tablets are prepared as described in Example 4, except that instead of 2-n-propyl-1-[(2'-n-propylaminocarbonylaminosulfonyl-biphenyl- 4-yl)methyl]-4-methylthio-imidazole- 5-carboxylic acid one of the following compounds is used:
ethyl 2-n-propyl-1-[(2'-n-propylaminocarbonylaminosulfonyl-biphenyl- 4-yl)methyl]-4-methylthio-imidazole-5-carboxylate or
ethyl 2-n-butyl-1-[(2'-n-propylaminocarbonylaminosulfonyl-biphenyl- 4-yl)methyl]-4-methylthio-imidazole-5-carboxylate,
2-n-butyl-1-[(2'-n-propylaminocarbonylaminosulfonylbiphenyl- 4-yl)methyl]-4-methylthio-imidazole-5-carboxylic acid,
5,7-dimethyl-3-[(2'-methoxycarbonylaminosulfonyl-biphenyl- 4-yl)methyl]-2-ethyl-imidazo[4,5-b]pyridine,
2-n-butyl-4-chloro-5-hydroxymethyl-1-[(2'-(1H-tetrazol-5-yl)-biphenyl-4-yl)methyl]-imidazole,
5,7-dimethyl-3-[(2'-tetrazol-biphenyl-4-yl)methyl] -imidazo[4,5-b]pyridine,
or the corresponding mono- or dipotassium salts are used.

EXAMPLE 10

An injection solution is prepared analogously to the instructions described in Example 8, except that instead of 2-n-propyl-1-[(2'-n-propylaminocarbonylsulfonylbiphenyl-4-yl)methyl]-4-methylthio-imidazole-5-carboxylic acid, the following substances are employed:
ethyl 2-n-propyl-1-[(2'-n-propylaminocarbonylaminosulfonyl-biphenyl- 4-yl)methyl]-4-methylthio-imidazole-5carboxylate,
ethyl 2-n-butyl-1-[(2'-n-propylaminocarbonylaminosulfonyl-biphenyl- 4-yl)methyl]-4-methylthio-imidazole-5carboxylate,
2-n-butyl-1-[(2'-n-propylaminocarbonylaminosulfonyl-biphenyl- 4-yl)methyl]-4-methylthio-imidazole-5-carboxylic acid,
5,7-dimethyl-3-[(2'-methoxycarbonylaminosulfonyl-biphenyl- 4-yl)methyl]-2-ethyl-imidazo[4,5-b]pyridine,
2-n-butyl-4-chloro-5-hydroxymethyl-1-[(2'-(1H-tetrazol-5-yl)-biphenyl-4-yl)methyl]-imidazole,
5,7-dimethyl-3-[(2'-tetrazol-biphenyl-4-yl)methyl]-imidazo [4,5-b]pyridine,
or the corresponding mono- or dipotassium salts.

We claim:
1. A method for the treatment of prophylaxis coronary heart disease in a mammal comprising the step of administering to a mammal in recognized need thereof an effective amount of an antagonist for angiotensin II receptors of the $AT_1$ subtype of the formula

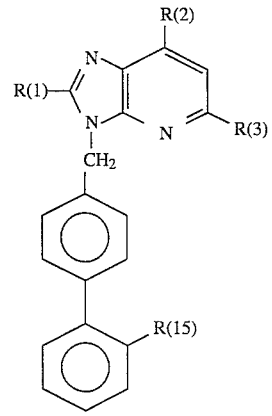

in which:

R(1) is $(C_1-C_7)$-alkyl, $(C_3-C_7)$-alkenyl or $(C_3-C_7)$-alkynyl;

R(2) and R(3) are the same or different and are hydrogen or $(C_1-C_4)$-alkyl;

R(15) is —SO—NR(18)—CO—OR(17), —SO$_2$—NR(18)—CO—NHR(16), —SO$_2$—NH—CO—R(17) or tetrazoyl;

R(16) and R(17) are the same and are $(C_1-C_4)$-alkyl, $(C_2-C_6)$alkenyl, $(C_3-C_8)$-cycloalkyl-$(C_1-C_4)$-alkyl, phenyl or phenyl-$(C_1-C_4)$-alkyl; and R(18) is hydrogen or $(C_1-C_6)$-alkyl; or a physiologically tolerable salt thereof.

2. The method as claimed in claim 1, wherein the antagonist is:

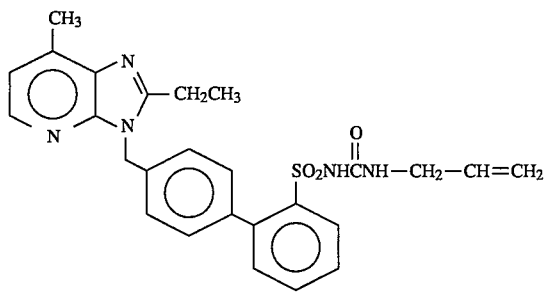

3. The method as claimed in claim 1, wherein

R(1) is $(C_1-C_4)$-alkyl;

R(15) is —SO—NR(18)—CO—OR(17) or —SO$_2$—NR(18)—CO—NHR (16);

R(16) and R(17) are the same and are $(C_1-C_4)$-alkyl, $(C_2-C_6)$alkenyl or $(C_3-C_8)$-cycloalkyl-$(C_1-C_4)$-alkyl;

R (18) is hydrogen; and the other radicals are as defined in claim 16.

4. The method as claimed in claim 3, wherein

R(15) is —SO$_2$—NR(18)—CO—NHR(16); and the other radicals are as defined in claim 17.

* * * * *

UNITED STATES PATENT AND TRADEMARK OFFICE
CERTIFICATE OF CORRECTION

PATENT NO. : 5,475,004
DATED : December 12, 1995
INVENTOR(S) : Holger HEITSCH et al.

It is certified that error appears in the above-indentified patent and that said Letters Patent is hereby corrected as shown below:

Claim 1, Column 38, Line 31, "of" should read --or--, and after "prophylaxis" insert --of--.

Claim 1, Column 38, Line 61, "tetrazoyl" should read --tetrazolyl--.

Signed and Sealed this

Twenty-seventh Day of August, 1996

Attest:

BRUCE LEHMAN

Attesting Officer        Commissioner of Patents and Trademarks